US008790393B2

(12) United States Patent
Bregulla et al.

(10) Patent No.: US 8,790,393 B2
(45) Date of Patent: Jul. 29, 2014

(54) HEAT-TREATED TANTALUM-ALLOY PRODUCTS, IMPLANTABLE MEDICAL DEVICES INCORPORATING SAME, AND METHODS OF PROCESSING TANTALUM-ALLOY PRODUCTS

(75) Inventors: Rainer Bregulla, Balingen (DE);
Randolf von Oepen, Aptos, CA (US);
Pamela A Kramer-Brown, San Jose, CA (US); Austin M Leach, Oakland, CA (US)

(73) Assignee: Abbott Cardiovascular Systems, Inc., Santa Clara, CA (US)

( * ) Notice: Subject to any disclaimer, the term of this patent is extended or adjusted under 35 U.S.C. 154(b) by 111 days.

(21) Appl. No.: 13/271,869

(22) Filed: Oct. 12, 2011

(65) Prior Publication Data
US 2013/0096667 A1    Apr. 18, 2013

(51) Int. Cl.
*A61F 2/91*    (2013.01)
(52) U.S. Cl.
USPC ........................................ 623/1.46; 623/1.44
(58) Field of Classification Search
USPC ................................ 623/1.34, 1.44, 1.46, 1.49
See application file for complete search history.

(56) References Cited

U.S. PATENT DOCUMENTS

| 5,716,400 | A * | 2/1998 | Davidson ................... 623/2.42 |
| 6,375,826 | B1 | 4/2002 | Wang et al. |
| 2007/0173925 | A1* | 7/2007 | Fliedner ..................... 623/1.15 |
| 2010/0222866 | A1 | 9/2010 | Wachter et al. |
| 2011/0264161 | A1* | 10/2011 | Schiefer et al. ................ 607/36 |

OTHER PUBLICATIONS

"Forging of Niobium, tantalum, and Their Alloys" MetalPass, accessed Apr. 18, 2013. http://www.metalpass.com/metaldoc/paper.aspx?docID=312.*
U.S. Appl. No. 13/548,908, filed Jul. 13, 2012, Lin.

* cited by examiner

*Primary Examiner* — Thomas J Sweet
*Assistant Examiner* — Rebecca Preston
(74) *Attorney, Agent, or Firm* — Workman Nydegger; John Kwok

(57) ABSTRACT

The present disclosure is directed to tantalum-alloy products, implantable medical devices that incorporate tantalum-alloy products such as stents or other implantable medical devices, methods of making and/or processing the tantalum-alloy products and implantable medical devices, and methods of using the implantable medical devices. In an embodiment, a stent includes a stent body having a plurality of struts. At least a portion of the stent body is made from a tantalum alloy. The tantalum alloy includes a tantalum content of about 77 weight % ("wt %") to about 92 wt %, a niobium content of about 7 wt % to about 13 wt %, and a tungsten content of about 1 wt % to about 10 wt %. The tantalum alloy exhibits at least one mechanical property modified by heat treatment thereof, such as yield strength, ultimate tensile strength, or ductility.

29 Claims, 16 Drawing Sheets

HEAT-TREATED TANTALUM-ALLOY PRODUCTS, IMPLANTABLE MEDICAL DEVICES INCORPORATING SAME, AND METHODS OF PROCESSING TANTALUM-ALLOY PRODUCTS

BACKGROUND

The human body includes various lumens, such as blood vessels or other passageways. A lumen may sometimes become at least partially blocked or weakened. For example, a lumen may be at least partially blocked by a tumor, by plaque, or both. An at least partially blocked lumen may be reopened or reinforced with an implantable stent.

A stent is typically a tubular body that is placed in a lumen in the body. A stent may be delivered inside the body by a catheter that supports the stent in a reduced-size configuration as the stent is delivered to a desired deployment site within the body. At the deployment site, the stent may be expanded so that, for example, the stent contacts the walls of the lumen to expand the lumen.

Advancement of the stent through the body may be monitored during deployment. After the stent is delivered to the target site, the stent can be monitored to determine whether the placement thereof is correct and/or the stent is functioning properly. Methods of tracking and monitoring stent after delivery include X-ray fluoroscopy and magnetic resonance imaging ("MRI").

Stents made from tantalum alloys have been identified as being easily detectable using X-ray fluoroscopy and MRI because of the high density of tantalum. Furthermore, tantalum alloys are typically compatible with MRI techniques because they do not produce substantial amounts of magnetic artifacts and/or image distortions or voids during MRI imaging. Additionally, tantalum alloys have proven to be biocompatible and corrosion resistant.

SUMMARY

The present disclosure is directed to tantalum-alloy products that exhibit sufficient radiopacity when imaged in a living subject, implantable medical devices (e.g., stents, guide wires, closure elements, etc.) that incorporate such tantalum-alloy products, and methods of processing such tantalum-alloy products to modify at least one of a microstructural, a mechanical, or a chemical property thereof. In an embodiment, a tantalum-alloy product is disclosed. The tantalum-alloy product includes a body comprising a tantalum alloy. The tantalum alloy includes a tantalum content of about 77 weight % ("wt %") to about 92 wt %, a niobium content of about 7 wt % to about 13 wt %, and a tungsten content of about 1 wt % to about 10 wt %. The tantalum alloy exhibits at least one mechanical property modified by heat treatment thereof.

In an embodiment, a tantalum-alloy product includes a body comprising a tantalum alloy. The tantalum alloy may exhibit a tensile elongation of about 5% to about 50%, a tensile yield strength of about 440 MPa to about 840 MPa, an ultimate tensile strength of about 490 MPa to about 880 MPa, and a radiopacity less than or equal to substantially pure tantalum having a thickness of about 55.88 µm (0.0022 inch).

In an embodiment, an implantable medical device is disclosed. The implantable medical device includes a body sized and configured to be implanted in a living subject. At least a portion of the body may comprise a tantalum alloy. The tantalum alloy includes tantalum content of about 77 wt % to about 92 wt %, a niobium content of about 7 wt % to about 13 wt %, and a tungsten content of about 1 wt % to about 10 wt %. The tantalum alloy exhibits at least one mechanical property modified by heat treatment thereof. In an embodiment, the body may be configured as a stent body, a guide wire, a closure device, embolic coils, pacemaker leads, sutures, prosthetic heart valves, mitral valve repair coils, or other implantable structure.

In an embodiment, an implantable medical device includes a body configured to be implanted into a living subject. At least a portion of the body may comprise a tantalum alloy. The tantalum alloy may exhibit a tensile elongation of about 5% to about 50%, a tensile yield strength of about 440 MPa to about 840 MPa, an ultimate tensile strength of about 490 MPa to about 880 MPa, and a radiopacity less than or equal to substantially pure tantalum having a thickness of about 55.88 µm (0.0022 inch). In an embodiment, the body may be configured as a stent body, a guide wire, a closure device, or other implantable structure.

In an embodiment, a method of processing a drawn tantalum-alloy product is disclosed. The method includes providing the drawn tantalum-alloy product. In an embodiment, the drawn tantalum-alloy product comprises a tantalum alloy having a tantalum content of about 77 wt % to about 92 wt %, a niobium content of about 7 wt % to about 13 wt %, and a tungsten content of about 1 wt % to about 10 wt %. In an embodiment, the drawn tantalum-alloy product may also be characterized by a tensile elongation of about 5% to about 50%, a tensile yield strength of about 440 MPa to about 840 MPa, an ultimate tensile strength of about 490 MPa to about 880 MPa, and a radiopacity less than or equal to substantially pure tantalum having a thickness of about 55.88 µm (0.0022 inch). The method further includes heat treating the drawn tantalum-alloy product to modify at least one mechanical property thereof.

In an embodiment, a method for implanting an implantable medical device (e.g., a stent) into a living subject is disclosed. The method includes delivering the implantable medical device in a delivery device to a selected deployment site within the living subject. In an embodiment, the implantable medical device comprises a tantalum alloy having a tantalum content of about 77 wt % to about 92 wt %, a niobium content of about 7 wt % to about 13 wt %, and a tungsten content of about 1 wt % to about 10 wt %. The tantalum alloy exhibits at least one mechanical property modified by heat treatment thereof. In an embodiment, the tantalum alloy may also be characterized by a tensile elongation of about 5% to about 50%, a tensile yield strength of about 440 MPa to about 840 MPa, an ultimate tensile strength of about 490 MPa to about 880 MPa, and a radiopacity less than or equal to substantially pure tantalum having a thickness of about 55.88 µm (0.0022 inch). The method further includes expanding the implantable device at the selected deployment site. The method additionally includes removing the implantable device from the delivery device.

Features from any of the disclosed embodiments may be used in combination with one another, without limitation. In addition, other features and advantages of the present disclosure will become apparent to those of ordinary skill in the art through consideration of the following detailed description and the accompanying drawings.

BRIEF DESCRIPTION OF THE DRAWINGS

To further clarify at least some of the advantages and features of the present disclosure, a more particular description of the disclosure will be rendered by reference to various embodiments thereof that are illustrated in the appended drawings. It is appreciated that these drawings depict only various embodiments of the disclosure and are therefore not to be considered limiting of its scope. The various embodiments will be described and explained with additional specificity and detail through the use of the accompanying drawings in which.

DETAILED DESCRIPTION

The present disclosure is directed to tantalum-alloy products that exhibit sufficient radiopacity when imaged in a living subject, implantable medical devices (e.g., stents) that incorporate such tantalum-alloy products, and methods of processing such tantalum-alloy products to enhance at least one of a microstructural, a mechanical, or a chemical property thereof. The tantalum-alloy products disclosed herein may be incorporated as all or part of an implantable medical device, such as a stent. The description below is directed mainly to a stent including a stent body made from a tantalum alloy that is composed and processed to impart at least one of certain microstructural, mechanical, or chemical properties to the tantalum alloy. However, other implantable medical devices besides stents may employ a tantalum alloy exhibiting one or more of the disclosed properties, such as guide wires, closure elements, or medical devices or potions thereof for deploying the foregoing medical devices.

Tantalum-Alloy Products, Such as Stents and Other Implantable Medical Devices

Figure 1A:
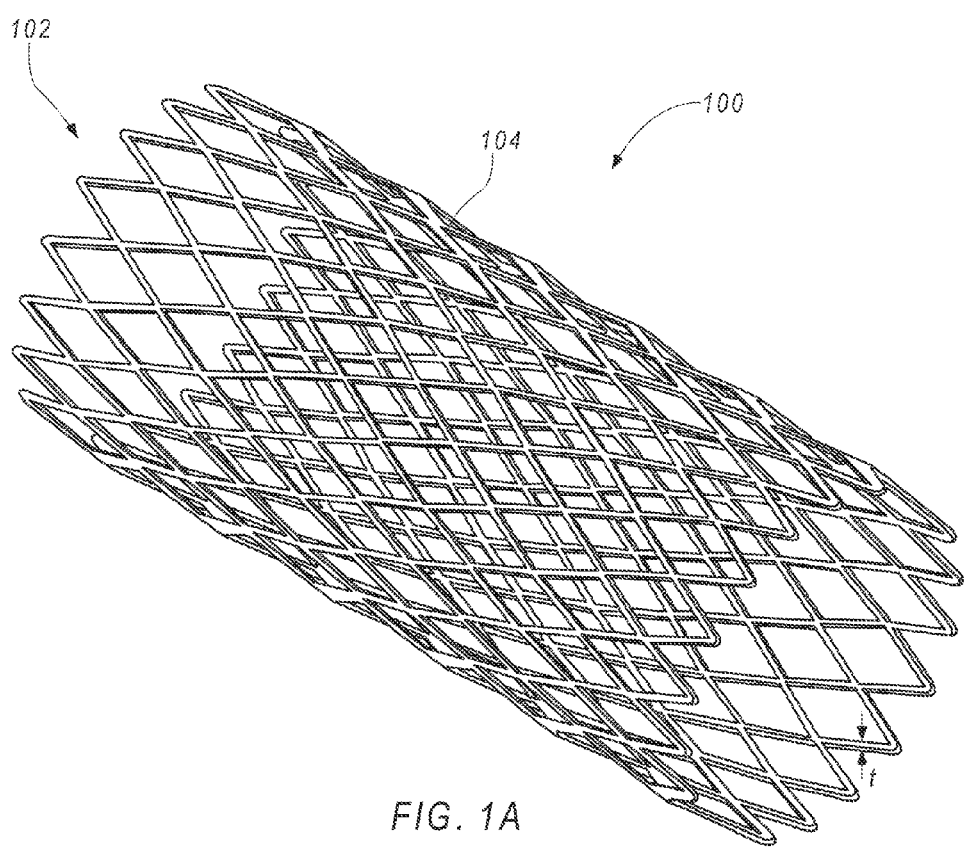
FIG. 1A is an isometric view of a stent made from a tantalum alloy according to an embodiment of the present disclosure.

FIG. 1A is an isometric view of a stent 100 made from a tantalum alloy according to an embodiment of the present disclosure. The stent 100 includes a stent body 102 sized and configured to be implanted and deployed into a lumen of a living subject. The stent body 102 may be defined by a plurality of interconnected struts 104 configured to allow the stent body 102 to radially expand and contract. However, it is noted that the illustrated configuration for the stent body 102 is merely one of many possible configurations, and other stent-body configurations made from the inventive tantalum-alloy products disclosed herein are encompassed by the present disclosure. For example, the struts 104 may be integrally formed with each other as shown in the illustrated embodiment, separate struts may be joined together by, for example, welding or other joining process, or separate stent sections may be joined together.

The stent body 102 is made from a tantalum alloy that is composed and heat-treated to obtain one or more of certain desirable microstructural, mechanical, or chemical properties. For example, the tantalum alloy may be heat treated to modify at least one mechanical property thereof, such as ductility, yield strength, or ultimate tensile strength. The tantalum alloy includes a tantalum content of about 77 wt % to about 92 wt %, a niobium content of about 7 wt % to about 13 wt % (e.g., about 7 wt % to about 12 wt %), and a tungsten content of about 1 wt % to about 10 wt %. However, the tantalum alloy may also include other alloying elements, such as one or more grain-refining elements in an amount up to about 5 wt % of the tantalum alloy. For example, the one or more grain-refining elements may include at least one of hafnium, cerium, or rhenium. Tungsten is provided to solid-solution strengthen tantalum, and niobium is provided to improve the ability of tantalum to be drawn. The tantalum alloy is a substantially single-phase, solid-solution alloy having a body-centered cubic crystal structure. However, some secondary phases may be present in small amounts (e.g., inclusions) depending upon the processing employed to fabricate the tantalum alloy.

The composition of the tantalum alloy may be selected from a number of alloy compositions according to various embodiments. In an embodiment, the niobium content is about 8 wt % to about 12 wt % (e.g., about 9 wt % to about 11 wt %), the tungsten content is about 6 wt % to about 9 wt % (e.g., about 6.5 wt % to about 8.5 wt %), and the balance may include tantalum (e.g., the tantalum content being about 80 wt % to about 83 wt %) and, if present, other minor alloying elements and/or impurities. In a more detailed embodiment, the niobium content is about 10 wt %, the tungsten content is about 7.5 wt %, and the balance may include tantalum (e.g., the tantalum content being about 82.5 wt %) and, if present, other minor alloying elements and/or impurities. In another more detailed embodiment, the niobium content is about 10 wt %, the tungsten content is about 2.5 wt %, and the balance may include tantalum (e.g., the tantalum content being about 87.5 wt %) and, if present, other minor alloying elements and/or impurities.

In another embodiment, the niobium content is about 10.5 wt % to about 13 wt %, the tungsten content is about 5.0 wt % to about 6 wt %, and the balance may include tantalum (e.g., the tantalum content being about 80 wt % to about 82 wt %) and, if present, other minor alloying elements and/or impurities. In a more detailed embodiment, the niobium content is about 12.5 wt %, the tungsten content is about 5.8 wt %, and the balance may include tantalum (e.g., the tantalum content being about 81 wt % to about 81.5 wt %) and, if present, other minor alloying elements and/or impurities.

In an embodiment, the tantalum alloy may exhibit a grain microstructure characteristic of being formed by heat treating a precursor product of the stent body 102 or the stent body 102 itself, both of which may be severely plastically deformed in a drawing process. Tantalum alloys readily oxidize and form an oxide layer on the inner and outer diameter surfaces during the tubing fabrication process. Such oxide layers can be removed by subjecting the tubes to a chemical etching process (e.g., in a solution of HF and $HNO_3$). The inventors in the present case have found that if the oxide layer is not removed prior to the heat treatment, the surface oxide can diffuse into the body of the alloy and decrease ductility, which can yield artificially high numbers for ultimate tensile strength and yield strength.

Depending upon the extent of recrystallization process, the grain microstructure may be only partially recrystallized. In some embodiments, the recrystallization process may substantially completely recrystallize the grain microstructure with the new recrystallized grains having consumed substantially all of the old deformed grains. Even when the grain microstructure is partially recrystallized, it will be apparent from microstructural analysis using optical and/or electron microscopy that the grain microstructure includes some recrystallized grains. An average grain size of the tantalum alloy may be about 10 μm to about 20 μm and, more particularly, about 13 μm to about 16 μm in the transverse orientation depending on the extent of recrystallization and the amount of the optional one or more grain-refining alloy elements in the tantalum alloy.

In other embodiments, the tantalum alloy may be stress relieved at a temperature below a recrystallization temperature of the tantalum alloy so that the grain microstructure is relatively unchanged from the as-drawn condition. Thus, in the stress-relieved condition, the grain microstructure may include essentially only non-equiaxed, deformed, cold-worked grains. However, the stress-relief heat treatment may at least partially remove at least one of hydrogen, oxygen, or nitrogen from the tantalum alloy, which can detrimentally embrittle the tantalum alloy. Thus, the tantalum alloy in the stress-relieved condition may exhibit an improved ductility relative to the as-drawn condition, while the tensile yield strength and tensile ultimate tensile strength may be relatively lowered by the stress-relief heat treatment.

The heat-treated tantalum alloy from which the stent body 102 is made may exhibit combination of strength (e.g., tensile yield strength and ultimate tensile strength) and ductility (e.g., percent elongation) suitable to withstand loading conditions encountered when implanted and utilized in a lumen of a living subject. The tensile yield strength may be the 0.2% offset yield strength determined in a uniaxial tensile test when no yield point is present, and the yield point if the tantalum alloy exhibits a yield point. For example, the heat treated tantalum alloy may exhibit a tensile elongation of about 5% to about 50%, a tensile yield strength of about 440 MPa to about 840 MPa, and an ultimate tensile strength of about 490 MPa to about 880 MPa as determined by, for example, tensile testing a tubular body from which the stent body 102 may be cut from or a drawn wire in a uniaxial tensile test. In an embodiment, the tantalum alloy (e.g., about 82.5 wt % tantalum, about 10 wt % niobium, and about 7.5 wt % tungsten) may exhibit a tensile elongation of about 9% to about 40%, a tensile yield strength of about 455 MPa to about 810 MPa, and an ultimate tensile strength of about 515 MPa to about 850 MPa. In another embodiment, the tantalum alloy may exhibit a tensile elongation of about 20% to about 40%, a tensile yield strength of about 460 MPa to about 480 MPa, and an ultimate tensile strength of about 500 MPa to about 520 MPa. In one embodiment, the tantalum alloy may exhibit a tensile elongation of about 23% to about 27%, a tensile yield strength of about 450 MPa to about 470 MPa, and an ultimate tensile strength of about 505 MPa to about 515 MPa.

In an embodiment, a heat-treated tantalum alloy from which the stent body 102 is made having a tantalum content of about 87.5 wt %, a niobium content of about 10 wt %, and a tungsten content of about 2.5 wt % and an at least partially recrystallized grain microstructure may exhibit a tensile elongation of about 5% to about 50%, a tensile yield strength of about 440 MPa to about 840 MPa, and an ultimate tensile strength of about 490 MPa to about 880 MPa. In one embodiment, the heat-treated tantalum alloy may exhibit a tensile elongation of about 20% to about 40%, a tensile yield strength of about 440 MPa to about 500 MPa, and an ultimate tensile strength of about 490 MPa to about 540 MPa.

In an embodiment, a stress-relieved tantalum alloy from which the stent body 102 is made having a tantalum content of about 82.5 wt %, a niobium content of about 10 wt %, and a tungsten content of about 7.5 wt % may exhibit a percent elongation of about 5% to about 15% (e.g., about 9% to about 11%), a tensile yield strength of about 580 MPa to about 840 MPa (e.g., about 680 MPa to about 810 MPa), and an ultimate tensile strength of about 600 MPa to about 880 MPa (e.g., about 715 MPa to about 850 MPa). In the stress-relieved condition, the percent elongation of the tantalum alloy may increase by at least about 100%, at least about 200%, at least about 300%, at least about 400%, or about 300% to about 400% compared to the same tantalum alloy in the as-drawn (i.e., un-stress-relieved condition), while the tensile yield strength and ultimate tensile strength are reduced. As yield strength and ultimate tensile strength go down, the ductility of the tantalum alloy tends to increase. The reduction in tensile yield strength and ultimate tensile strength and the increase in ductility needs to be balanced, but, in general, increasing ductility tends to yield a more durable medical device fabricated from the tantalum alloy. For example, an alloy having increased ductility is less likely to crack when radially stressed. The grain microstructure may also be relatively unchanged from the as-drawn condition and may include deformed, non-equiaxed grains.

Other mechanical properties of the stent body 102 suitable for characterizing the combination of strength and ductility exhibited by the tantalum alloy include, but are not limited to, percent recoil and radial strength of the stent body 102. Such mechanical properties may be determined by crimping the stent body 102 on a mandrel, expanding the crimped stent body 102 to a specific outer diameter using a balloon catheter or a similar device, and inflating the expanded and crimped stent body 102 to a specific pressure. ASTM F2079 provides one suitable standard for determining percent recoil of the stent body 102. Radial strength may be determined using a commercially available machine for radially expanding a stent, such as an MSI radial strength tester. For example, the percent recoil may be about 1% to about 5% (e.g., about 2% to about 3%) and the radial strength may be about 845 mm Hg to about 1050 mm Hg (e.g., about 880 mm Hg to about 1000 mm Hg) when the stent 100 is expanded to an outer diameter of at least about 3 mm (e.g., about 3 mm to about 7 mm). More particularly, the percent recoil may be about 2.5% to about 3.2% and the radial strength may be about 950 mm Hg to about 1000 mm Hg when the stent 100 is expanded to an outer diameter of at least about 3 mm (e.g., about 3 mm to about 7 mm).

The disclosed heat-treated tantalum alloys are sufficiently radiopaque and stronger (e.g., greater yield strength) than substantially pure tantalum (e.g., commercially pure tantalum). Consequently, the struts 104 of the stent body 102 may be thinner in a radial direction than a stent made from substantially pure tantalum and having a similar configuration, while still providing adequate imaging characteristics under X-ray fluoroscopy and MRI. Commercially pure tantalum exhibits a relatively greater radiopacity. However, since commercially pure tantalum is much weaker than the tantalum alloys disclosed herein, a stent made from commercially pure tantalum typically could be excessively thick for structural reasons thereby resulting in the stent being excessively radiopaque and making it difficult to distinguish surrounding body tissue during imaging.

Referring still to FIG. 1A, for example, an average thickness "t" of the struts 104 of the stent body 102 in a radial direction may be about 40 μm to about 100 μm, about 60 μm to about 80 μm (e.g., about 70 μm), about 50 μm to about 90 μm, about 50 lam to about 77 μm, about 53 μm to about 68.5 μm, or about 58 μm to about 63.5 μm, while also exhibiting the desirable disclosed combination of strength, ductility, and radiopacity as discussed hereinabove. Because the disclosed heat-treated tantalum alloys are sufficiently strong as characterized by yield strength, ultimate tensile strength, radial strength, or combinations of the foregoing mechanical properties, the average thickness "t" of the struts 104 of the stent body 102 may be made sufficiently thin to help reduce vessel injury and enhance deliverability while still having a sufficient radiopacity to be visible in X-ray fluoroscopy and MRI.

In an embodiment, for a thickness of about 60.96 μm (0.0024 inch), any of the tantalum alloy embodiments disclosed herein may have a radiopacity about equal to a radiopacity of substantially pure tantalum having a thickness of about 55.88 μm (0.0022 inch). In other embodiments, for a thickness about equal to or less than about 60.96 μm (0.0024 inch), any of the tantalum alloy embodiments disclosed herein may have a radiopacity of about 101% or less, about 100% or less, about 98% or less, about 95% or less, 93% or less, about 90% or less, or about 85% or less than the radiopacity of substantially pure tantalum having a thickness of 55.88 μm (0.0022 inch) and measured using cine equipment with an x-ray energy value of about 80 kVp to about 120 kVp. Radiopacity may be calculated by the equation Radiopacity=$e^{\mu_{ave} x}$, where $\mu_{ave}$ is the average linear attenuation coefficient for the tantalum alloy of interest or substantially pure tantalum and for a particular incident X-ray energy, and X is thickness.

In one or more embodiments, the stent body 102 may be etched in an acid (e.g., hydrofluoric acid) to remove features (e.g., slag, remelt, heat-affected zones, etc) associated with forming the struts 104 via laser cutting and/or electropolished to improve a surface finish of the stent body 102. In such embodiments, the stent body 102 may be heat treated (e.g., a stress-relief heat treatment and/or recrystallization heat treatment) so that at least one of hydrogen, oxygen, or nitrogen introduced to the tantalum alloy from the acid and/or the electropolishing solution is at least partially removed. Following heat treatment, the stent body 102 may include one or more etched and/or one or more electropolished surfaces, and the tantalum alloy that forms the stent body 102 may substantially free of at least one of hydrogen, oxygen, or nitrogen or include at least one of hydrogen, oxygen, or nitrogen in an amount below a threshold concentration sufficient to cause environmental cracking in the tantalum alloy, such as hydrogen that causes hydrogen embrittlement. For example, oxygen may be present in the tantalum alloy in a concentration of about 400 ppm or less (e.g., about 100 ppm to about 300 ppm) without causing embrittlement.

Figure 1B:
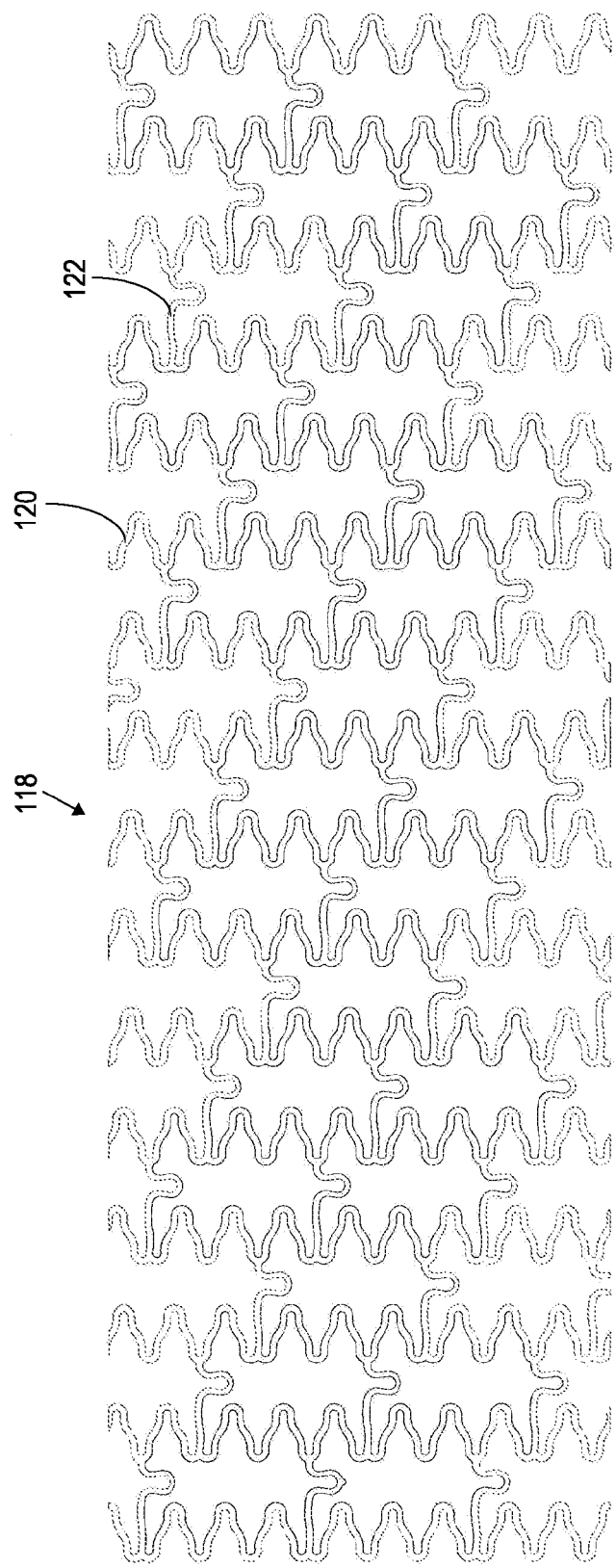
FIG. 1B illustrates a strut design for a stent made from a tantalum alloy according to an embodiment of the present disclosure.

FIG. 1B illustrates a strut design for another stent 118 that can be made from a tantalum alloy according to an embodiment of the present disclosure. The stent 118 includes a number of interconnected strut elements 120 and connector elements 122 that connect adjacent strut elements. The stent 118 can be sized and configured to be implanted and deployed into a lumen of a living subject. However, it is noted that the illustrated configuration for the stent 118 is merely one of many possible configurations, and other stent-body configurations made from the inventive tantalum-alloy products disclosed herein are encompassed by the present disclosure.

As in the previous example, the stent 118 is made from a tantalum alloy that is composed and heat-treated to obtain one or more of certain desirable microstructural, mechanical, or chemical properties. For example, the tantalum alloy may be heat treated to modify at least one mechanical property thereof, such as ductility, yield strength, or ultimate tensile strength. The tantalum alloy includes a tantalum content of about 77 wt % to about 92 wt %, a niobium content of about 7 wt % to about 13 wt % (e.g., about 7 wt % to about 12 wt %), and a tungsten content of about 1 wt % to about 10 wt %. However, the tantalum alloy may also include other alloying elements, such as one or more grain-refining elements in an amount up to about 5 wt % of the tantalum alloy. For example, the one or more grain-refining elements may include at least one of hafnium, cerium, or rhenium. Tungsten is provided to solid-solution strengthen tantalum, and niobium is provided to improve the ability of tantalum to be drawn. The tantalum alloy is a substantially single-phase, solid-solution alloy having a body-centered cubic crystal structure. However, some secondary phases may be present in small amounts (e.g., inclusions) depending upon the processing employed to fabricate the tantalum alloy.

The composition of the tantalum alloy may be selected from a number of alloy compositions according to various embodiments. In an embodiment, the niobium content is about 8 wt % to about 12 wt % (e.g., about 9 wt % to about 11 wt %), the tungsten content is about 6 wt % to about 9 wt % (e.g., about 6.5 wt % to about 8.5 wt %), and the balance may include tantalum (e.g., the tantalum content being about 80 wt % to about 83 wt %) and, if present, other minor alloying elements and/or impurities.

In one embodiment, the tantalum alloy used to form the stent 118 may be heat treated as described above with reference to stent 100. As a result, the tantalum alloy used to form stent 118 should have substantially the same tensile and elongation properties as the alloy described with reference to stent 100.

Other mechanical properties of the stent 118 suitable for characterizing the combination of strength and ductility exhibited by the tantalum alloy include, but are not limited to, percent recoil and radial strength of the stent 118. Such mechanical properties may be determined by crimping the stent 118 on a mandrel, expanding the crimped stent 118 to a specific outer diameter with a balloon or a similar device, and inflating the expanded and crimped stent body 102 to a specific pressure. ASTM F2079 provides one suitable standard for determining percent recoil of the stent 118. Radial strength may be determined using a commercially available machine for radially expanding a stent, such as an MSI radial strength tester. For example, the percent recoil for this stent design may be about 1% to about 5% (e.g., about 2% to about 4%) and the radial strength may be about 1000 mm Hg to about 880 mm Hg (e.g., about 950 mm Hg to about 880 mm Hg) when the stent 118 is expanded to an outer diameter of about 3 mm (e.g., about 3 mm to about 7 mm). More particularly, the percent recoil may be about 2% to about 3% and the radial strength may be about 950 mm Hg to about 880 mm Hg when the stent 118 is expanded to an outer diameter of about 3 mm.

In one or more embodiments, the stent 118 may be etched in an acid (e.g., hydrofluoric acid) to remove features associated with forming the struts 120 and connectors 122 via laser cutting and/or electropolished to improve a surface finish of the stent 118. In such embodiments, the stent 118 may be heat treated (e.g., a stress-relief heat treatment and/or recrystallization heat treatment) so that at least one of hydrogen, oxygen, or nitrogen introduced to the tantalum alloy from the acid and/or the electropolishing solution is at least partially removed. Following heat treatment, the stent 118 may include one or more etched and/or one or more electropolished surfaces, and the tantalum alloy that forms the stent 118 may substantially free of at least one of hydrogen, oxygen, or nitrogen or include at least one of hydrogen, oxygen, or nitrogen in an amount below a threshold concentration sufficient to cause environmental cracking in the tantalum alloy, such as hydrogen that causes hydrogen embrittlement. For example, oxygen may be present in the tantalum alloy in a concentration of about 400 ppm or less (e.g., about 100 ppm to about 300 ppm) without causing embrittlement.

Figure 1C:
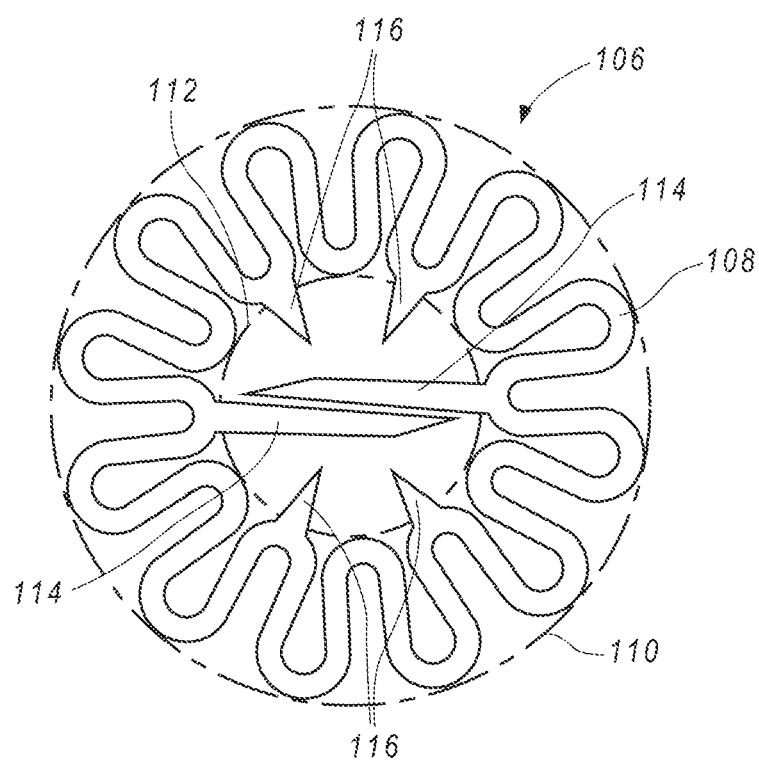
FIG. 1C is a plan view a closure element made from any of the tantalum alloys disclosed herein according to an embodiment of the present disclosure.
Figure 2:
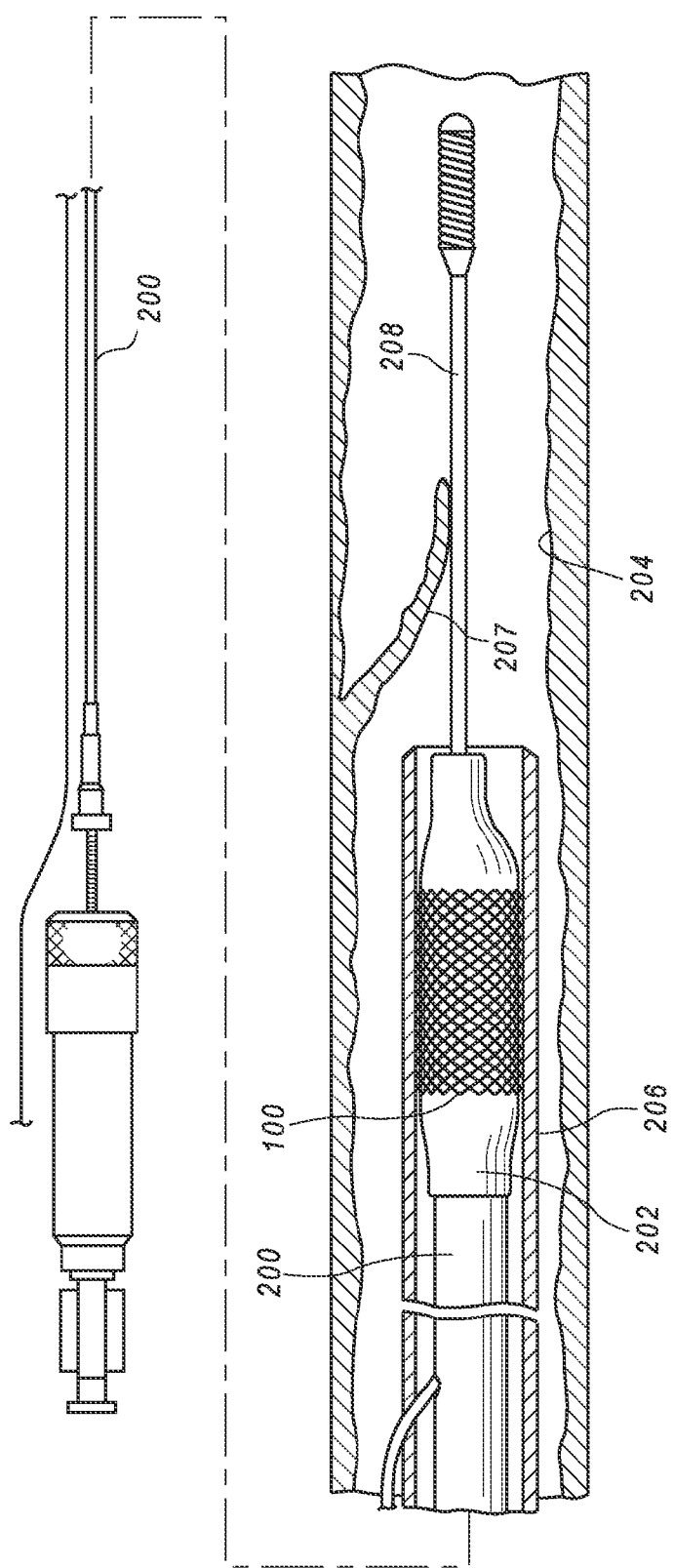
FIG. 2 is a side elevation view, in partial cross-section, of a delivery catheter within a body lumen having a stent disposed about the delivery catheter according to an embodiment of the present disclosure.

Other implantable medical devices besides stents may employ a tantalum alloy exhibiting one or more of the disclosed tailored properties, such as guide wires, closure elements, pacemaker leads, orthopedic devices, embolic coils, sutures, prosthetic heart valves, mitral valve repair coils, or other medical devices or portions thereof for deploying the foregoing medical devices. For example, FIG. 1C illustrates a closure element 106 (e.g., a staple) made from any of the heat-treated tantalum alloys disclosed herein. The closure element 106 includes a body 108 defining an outer perimeter 110, an inner perimeter 112, primary tines 114, and secondary tines 116. A guide wire 208 is shown in FIG. 2 configured to facilitate deploying the stent 100 and may be made from any of the heat-treated tantalum alloys disclosed herein. Other embodiments of the present disclosure include a stent body in which one or more radiopaque marker elements may be formed from tantalum-alloy products composed and processed as disclosed herein, and such markers may form only part of the stent body. Moreover, although the illustrated embodiment shown in FIGS. 1A and 1B depict stents 102 and 118 formed by cutting a tantalum-alloy tube to define the struts 104 and 120 and connectors 122, other embodiments for fabricating a stent body are contemplated. For example, a drawn wire made from any of the disclosed tantalum alloys may be heat treated as described herein, and formed into a tubular stent structure by at least one of knitting, coiling weaving, or welding one or more of such drawn/heat treated wires.

Embodiments of Methods for Stent Deployment

Implantable medical devices disclosed herein, such as the stent 100 shown in FIG. 1A, may be delivered into a body of a living subject by a number of different techniques. For example, a delivery catheter may be employed to deliver and deploy the stent 100. An embodiment of a method for delivering an implantable medical device into a body lumen of a living subject may include: (1) providing a stent as disclosed herein; (2) delivering the stent to a desired deployment site within the body lumen of the living subject; (3) expanding the stent so that it applies a radially outward force to an inner wall of the body lumen.

FIG. 2 is a side elevation view, in partial cross-section, of a delivery catheter 200 having with the stent 100 disposed thereabout according to an embodiment of the present disclosure, which provides more detail about the manner in which the stent 100 may be inserted and deployed within a living subject. The delivery catheter 200 has an expandable member or balloon 202 for expanding the stent 100, on which the stent 100 is mounted, within a body lumen 204 such as an artery. For example, the body lumen 204, as shown in FIG. 2, may have a dissected lining 206 that has occluded a portion of the body lumen 204.

The delivery catheter 200 may be a conventional balloon dilatation catheter commonly used for angioplasty procedures. The balloon 202 may be formed of, for example, polyethylene, polyethylene terephthalate, polyvinylchloride, nylon, or another suitable polymeric material. To facilitate the stent 100 remaining in place on the balloon 202 during delivery to the site of the damage within the body lumen 204, the stent 100 may be compressed onto the balloon 202. Other techniques for securing the stent 100 onto the balloon 202 may also be used, such as providing collars or ridges on edges of a working portion (i.e., a cylindrical portion) of the balloon 202.

In use, the stent 100 may be mounted onto the inflatable balloon 202 on the distal extremity of the delivery catheter 200. The balloon 202 may be slightly inflated to secure the stent 100 onto an exterior of the balloon 202. The catheter/stent assembly may be introduced within a living subject using a conventional Seldinger technique through a guiding catheter 206. A guide wire 208 may be disposed across the damaged arterial section with the detached or dissected lining 207 and then the catheter/stent assembly may be advanced over the guide wire 208 within the body lumen 204 until the stent 100 is directly under the detached lining 207. For example, the guide wire 208 may be made from a superelastic nickel-titanium alloy, any of the heat-treated tantalum alloys disclosed herein, or another suitable material. The balloon 202 of the catheter 200 may be expanded, expanding the stent 100 against the interior surface defining the body lumen 204 by, for example, permanent plastic deformation of the stent 100. When deployed, the stent 100 holds open the body lumen 204 after the catheter 200 and the balloon 202 are withdrawn.

Embodiments of Methods for Making
Tantalum-Alloy Products and Furnace System

Referring again to FIG. 1A, the stent 100 may be manufactured in accordance with various embodiments of the present disclosure. In an embodiment of a method, a precursor drawn tantalum-alloy tube (i.e., a drawn tantalum-alloy product) or the stent body 102 made from a tantalum alloy having any of the tantalum alloy compositions disclosed herein may be provided. The drawn tantalum-alloy tube from which the stent body 102 is made may be formed in a drawing process and, consequently, is severely cold worked. For example, the drawn tantalum-alloy tube may exhibit about 70% to about 100% cold work, about 75% to about 100% cold work, about 80% to about 90% cold work, or about 95% to about 99% cold work.

The drawn tantalum-alloy tube or the stent body 102 may be heat treated at a temperature and for a time sufficient to at least partially recrystallize the grain microstructure of the tantalum alloy to impart the above-described mechanical properties to the tantalum alloy. In some embodiments, the drawn tantalum-alloy tube or the stent body 102 of the stent 118 may be etched in a chemical etching solution (e.g., a solution containing HF and $HNO_3$) prior to heat treating in order to remove an oxide layer present on the drawn tantalum-alloy tube or the stent body 102. The heat treatment may be performed in a vacuum furnace at a vacuum level of about $1 \times 10^{-4}$ torr to $1 \times 10^{-6}$ torr to help prevent impurities from dissolving in and/or reacting with the tantalum alloy. In an embodiment, the temperature and the time may be selected so that the grain microstructure is only partially recrystallized. In another embodiment, the temperature and the time may be selected so that the grain microstructure is substantially completely recrystallized. In such an embodiment, the recrystallization process may be terminated before proceeding past the stage of complete recrystallization. In yet another embodiment, the temperature and the time may be selected so that the grain microstructure includes grains having experienced grain growth characteristic of the heat-treatment process proceeding past the stage of complete recrystallization.

In an embodiment, the heat-treatment temperature is selected to be above the recrystallization temperature of the tantalum alloy. In various embodiments, the heat-treatment temperature may be about 1000° C. to about 1350° C., 1200° C. to about 1350° C., about 1250° C. to about 1300° C., or about 1275° C. While it is difficult to precisely determine the recrystallization temperature of the tantalum alloys disclosed herein, it is currently believed that the recrystallization temperature is about 1275° C., but it may be lower in tantalum alloys having relatively lower amounts of tungsten. The heat-treatment time may vary depending upon the extent of recrystallization and grain size that is desired in the tantalum alloy of the drawn tantalum-alloy tube. The heat-treatment time may be about 2 min to about 100 min, about 5 min to about 50 min, about 5 min to about 40 min, about 5 min to about 15, about 5 min to about 10 min, or about 6 min to about 8 min for any of the disclosed heat-treatment temperatures. In a specific embodiment, the heat treatment time may be about 40 min at 1275° C. The heat-treatment time may be the time at which the drawn tantalum-alloy tube is at a selected heat-treatment temperature and does not include the heat-up time necessary for the drawn tantalum-alloy tube to reach the heat-treatment temperature. The recrystallization time may decrease as the tungsten content in the disclosed tantalum alloys decreases.

Heat treating a tantalum alloy having about 80 wt % to about 83 wt % tantalum (e.g., about 82.5%), about 8 wt % to about 12 wt % niobium (e.g., about 10 wt %), and about 6 wt % to about 9 wt % tungsten (e.g., about 7.5 wt %) at about 1250° C. to about 1300° C. (e.g., about 1275° C.) for about 5 min to about 180 min (e.g., about 20 min to about 180 min or about 20 min to about 80 min) may provide for a combination of tensile strength properties and ductility that is suitable for the stent 100. For example, such tantalum alloys subjected to one or more of the aforementioned heat-treatment processes may exhibit a tensile elongation of about 20% to about 50% (e.g., about 23% to about 27%), a tensile yield strength of about 440 MPa to about 500 MPa (e.g., about 460 MPa to about 480 MPa), and an ultimate tensile strength of about 490 MPa to about 540 MPa (e.g., about 500 MPa to about 515 MPa).

Before or after heat treatment, the drawn tantalum-alloy tube may be cut using, for example, a laser-cutting process, electro-discharge machining, or another suitable cutting process to form the stent body 102 shown in FIG. 1A having the struts 104 formed therein.

In an embodiment, the drawn tantalum-alloy tube may be electropolished to polish exterior and interior surfaces thereof prior to the stent body 102 being formed therefrom. In another embodiment, after being formed, the stent body 102 may be electropolished and/or chemically etched in an acid (e.g., hydrofluoric acid) to remove features (e.g., heat-affected zones, slag, remelt, and the like) associated with defining the struts 104 of the stent body 102 via laser cutting. In such embodiments, the electropolished tantalum-alloy tube or the electropolished and/or etched stent body 102 may be heat treated at a temperature below a recrystallization temperature of the tantalum alloy to remove at least a portion of at least one of hydrogen, nitrogen, or oxygen dissolved in the tantalum alloy from the electropolishing solution used in the electropolishing process and/or the acid. Such a heat treatment is referred to as a stress-relief heat treatment.

For example, the stress relief heat treatment may be performed at a temperature of about 700° C. to about 1100° C., more particularly about 700° C. to about 1000° C., and even more particularly about 1000° C. After heat treatment, the tantalum alloy may be substantially free of at least one of hydrogen, nitrogen, or oxygen or may include at least one of hydrogen, oxygen, or nitrogen present below a threshold concentration sufficient to cause environmental cracking in the tantalum alloy, such as hydrogen that causes hydrogen embrittlement. Removal of at least one of hydrogen, nitrogen, or oxygen by a stress-relief heat treatment may substantially improve the ductility of the tantalum alloy, while reducing the yield strength and ultimate tensile strength compared to the as-drawn condition.

For example, in the stress-relieved condition, the tantalum alloy may exhibit a percent elongation of about 5% to about 15% (e.g., about 9% to about 11%), a yield strength of about 580 MPa to about 840 MPa (e.g., about 680 MPa to about 810 MPa), and an ultimate tensile strength of about 600 MPa to about 880 MPa (e.g., about 715 MPa to about 850 MPa). In the stress-relieved condition, the percent elongation may increase by about 200% to about 1200% or about 300% to about 1200%. In another embodiment, the percent elongation may increase by at least about 100%, at least about 200%, at least about 300%, at least about 400%, or about 200% to about 400% compared to the same tantalum alloy in the as-drawn (i.e., un-stress-relieved) condition, while the yield strength and ultimate tensile strength are reduced. It is noted that heat treating at a temperature sufficient to at least partially relieve the stress of the tantalum alloy may also at least partially remove at least one of hydrogen, nitrogen, or oxygen.

It is also noted that stress relief heat treatment may be performed after recrystallization heat treatment to relieve cold work and other stresses imparted on the material during stent fabrication and to remove embrittling gasses such as hydrogen, oxygen, and nitrogen that may become dissolved in the material during one or more manufacturing processes. Such a material that has been recrystallization heat treated and then at a later stage stress relief heat treated will have typically have elongation and tensile properties similar to metal that has been subjected to recrystallization heat treatment alone.

Electropolishing of the stent body 102 may be performed by immersing the stent body 102 in a temperature-controlled bath of electrolyte, and connecting a positive terminal (anode) of a direct current ("DC") power supply to the stent body 102 and a negative terminal of the DC power supply to an auxiliary electrode (cathode). A current passes from the anode to the cathode through the electrolyte solution. At the anode, metal on the surface of the stent body 102 is oxidized and dissolved in the electrolyte. At the cathode a reduction reaction takes place, which normally evolves hydrogen. Electrolytes used for electropolishing are most often concentrated acid solutions. To achieve electropolishing of a rough metal surface, the protruding portions of a surface profile dissolve faster than the recesses. This behavior, which is referred to as anodic leveling, may be achieved by applying a specific electrochemical condition (e.g., voltage, current, and/or acid concentration/acid makeup). In addition to smoothing the surface of the stent body 102, electropolishing may be used to adjust the dimension "t"s of the struts 104 to a desired size (e.g., about 58 μm to about 70 μm). In an alternative embodiment, the surface of the stent body 102 may be smoothed and the dimensions of the struts adjusted to the desired size using abrasive techniques such as bead blasting and the like.

In an embodiment, the electrolyte solution employed in the electropolishing may be an inaqueous acidic solution. For example, the electrolyte solution may contain methanol (or another alcohol), sulfuric acid ("$H_2SO_4$"), methanolic hydrochloric acid (methanol HCl) and, optionally, a desiccating agent such as polyethylene glycol ("PEG") and/or ethylene glycol. In another example, the electrolyte solution may contain methanol, $H_2SO_4$, and ethylene glycol. In a specific embodiment, the $H_2SO_4$ concentration in the electrolyte solution is about 1.5 molar ("M") to about 3 M (e.g., about 1.9 M), and the ethylene glycol concentration is about 0.8 M to about 1.1 M (e.g., about 0.9 M).

The stent body 102 may be electropolished in the electrolyte solution (i.e., methanol, $H_2SO_4$, and ethylene glycol) using a threshold current of up to about 4 amps. Preferably, the current is about 1 amp to about 3 amps, about 1.2 amps to about 2 amps, about 1.3 to about 1.6 amps, or about 1.5 amps.

The electrical current directed through the electrolyte solution is above the threshold current in order to achieve a smoothing or polishing effect on the surface of the stent body 102 as opposed to an roughening or etching effect. At lower current (e.g., about 1.5 amps) better surface finish is obtained and less damage to the stents is observed. As the electropolishing process proceeds, $H_2SO_4$ is consumed producing $H_2$ gas and metal sulfates. Eventually, as the $H_2SO_4$ is consumed, the current will drop below the threshold value. When the current drops below the threshold value, the solution needs should discarded. 800 ml of electrolyte solution is, for example, sufficient for electropolishing about 80 tantalum-alloy stents.

While the electrolyte solution is essentially water-free in the as-prepared condition, the solution is hygroscopic and can scavenge water out of the environment. In the case of the tantalum alloys discussed herein, the electrolyte solution is formulated to be essentially water-free because water reacts the tantalum and forms an oxide passivation layer on the surface of the tantalum alloy that can interfere with the electropolishing process. In one embodiment, a desiccating agent may be added to the electropolishing electrolyte solution to mitigate the effect of water that may be introduced into the electrolyte from the atmosphere or through the chemical action of the electropolishing process. PEG, ethylene glycol, and similar desiccating agents are capable of forming multiple hydrogen bonding interactions, which may surround and effectively sequester water that may otherwise interfere with the electropolishing process.

At least one of hydrogen, nitrogen, or oxygen may also be introduced to the tantalum alloy during the drawing process used to form the precursor drawn tantalum-alloy tube. As an alternative or in addition to heat treating after electropolishing and/or chemical etching, in another embodiment, the precursor drawn tantalum-alloy tube and/or the stent body 102 may be heat treated to at least partially remove at least a portion of hydrogen, nitrogen, and/or oxygen dissolved in the tantalum alloy that was introduced during the drawing process used to form the precursor drawn tantalum-alloy tube.

Figure 3A:
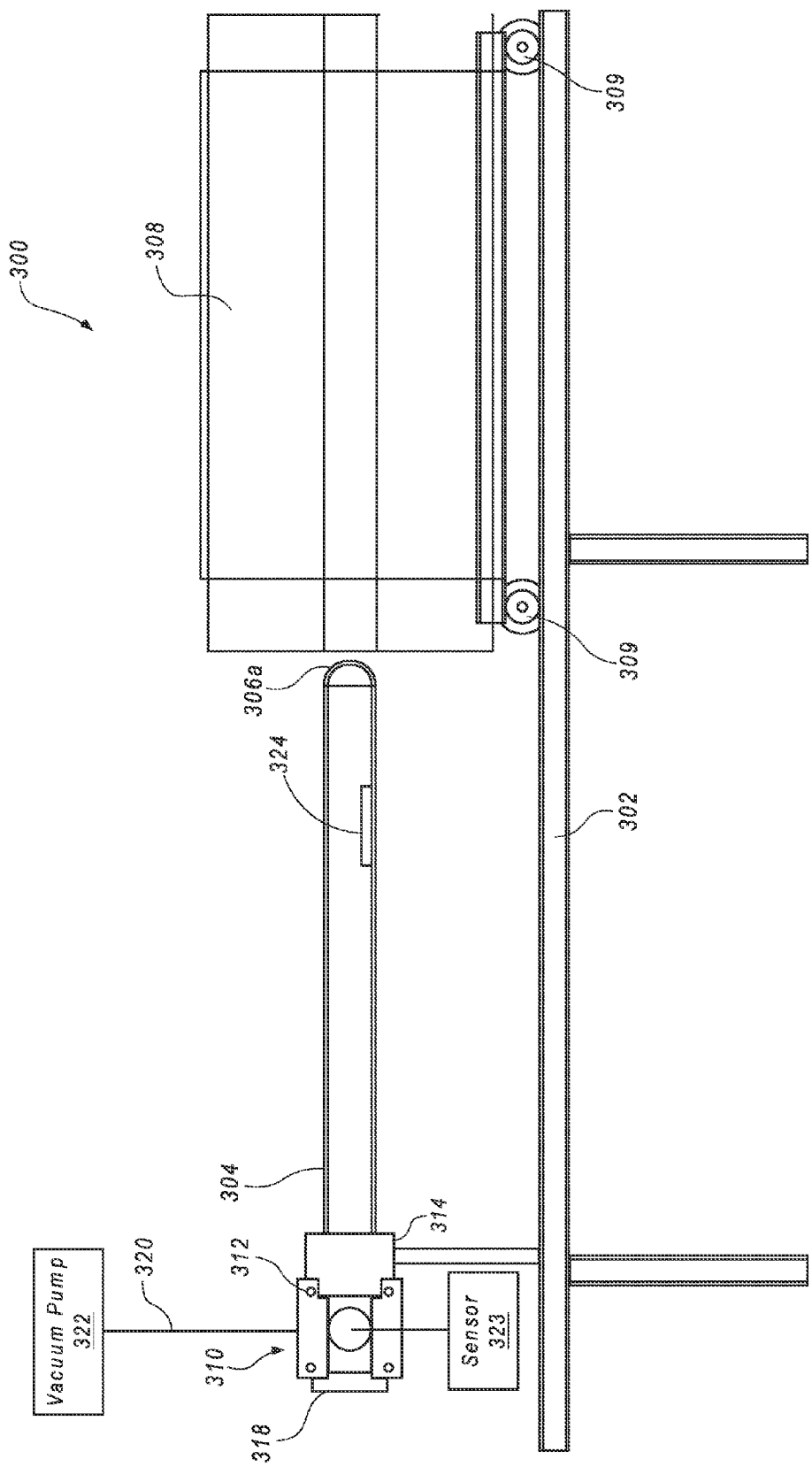
FIG. 3A is a side elevation view of a furnace system, suitable for heat treating a drawn tantalum-alloy product or stent incorporating such a product, with the heating element in a retracted position.
Figure 3B:
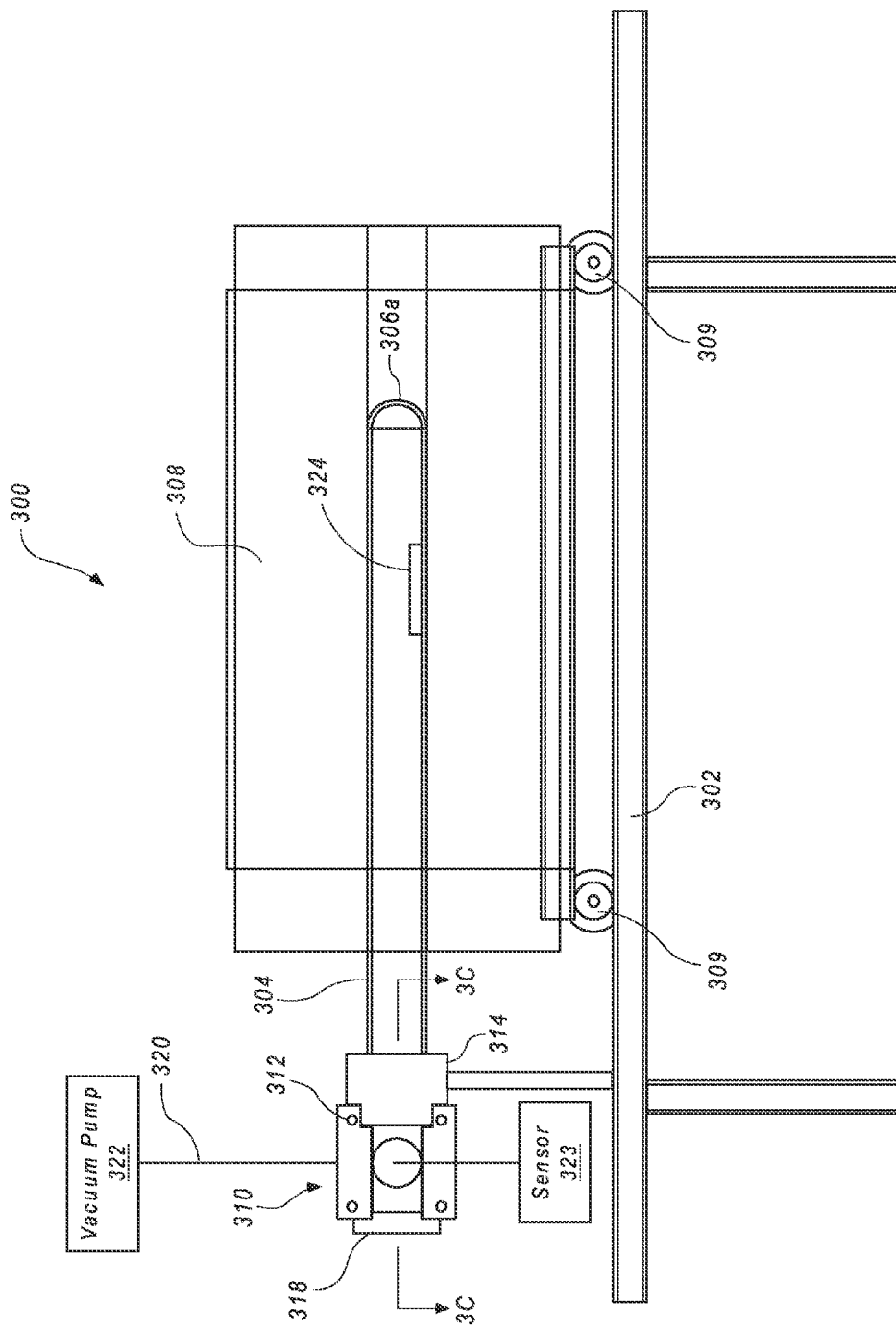
FIG. 3B is a side elevation view of the furnace system shown in FIG. 3A, with the heating element positioned over the furnace tube in a heating position.
Figure 3C:
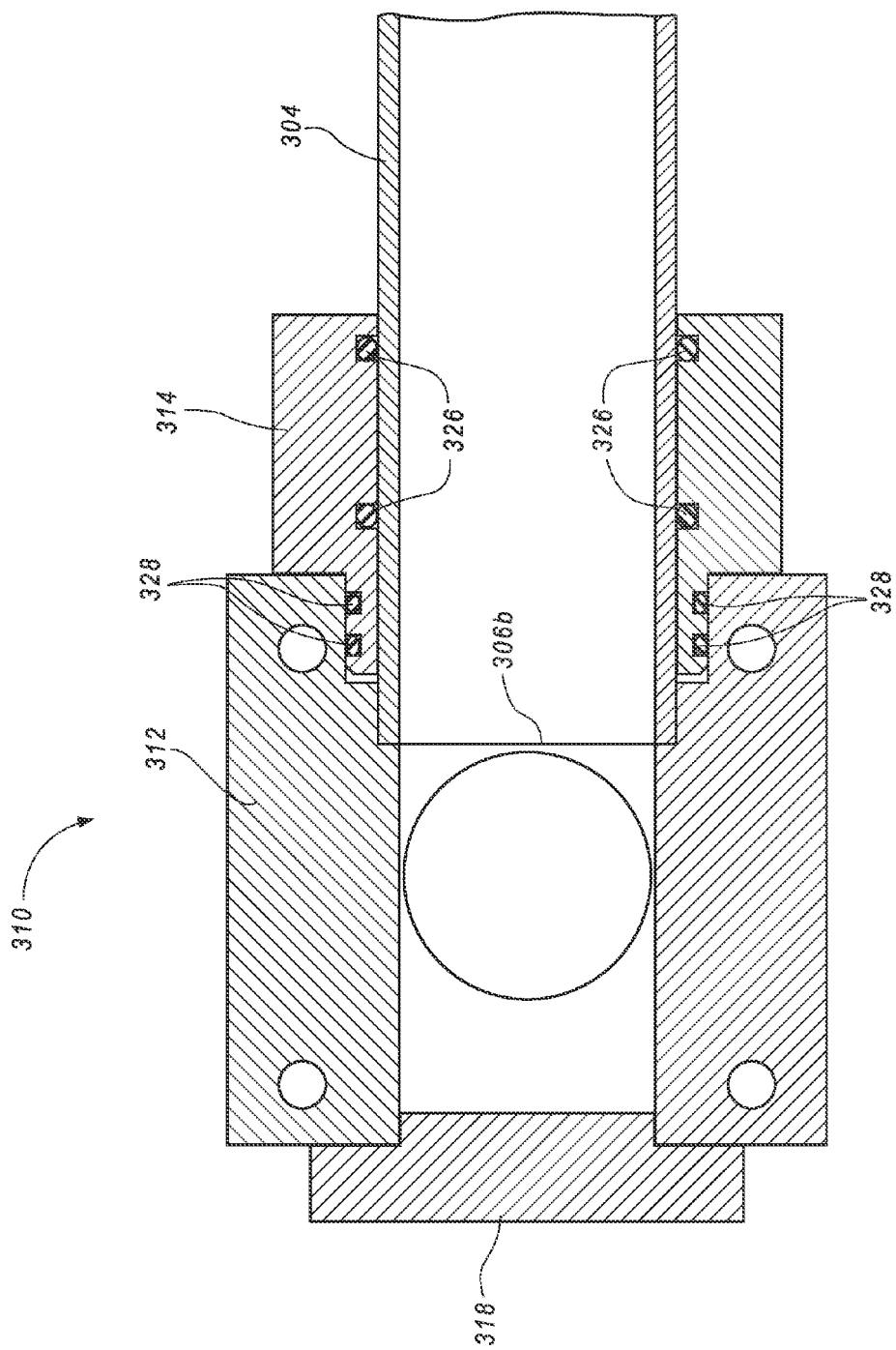
FIG. 3C is an enlarged cross-sectional view of the interlock assembly of the furnace system taken along line 3C-3C shown in FIG. 3B.

FIGS. 3A-3C illustrate an embodiment of a furnace system 300 suitable for heat treating the tantalum alloy from which the drawn tantalum-alloy products or stents described hereinabove are made. In other embodiments, other types of furnaces can be used. For example, vacuum furnaces used in the semiconductor manufacturing industry can be used in lie or in addition to furnace system 300. FIGS. 3A and 3B are side elevation views of the furnace system 300. The furnace system 300 may be supported on a support 302, such as a frame, a table, or other support structure. The furnace system 300 includes a furnace tube 304 having a closed end 306a and an opposing open end 306b (FIG. 3C). The furnace tube 304 may be made from a quartz glass, aluminum oxide, or other suitable material. The furnace system 300 further includes a heating element 308, which is represented as a furnace shroud in which the heating element is enclosed. For example, the heating element 308 may be a silicon carbide heating element, a molybdenum disilicide heating element, or another suitable heating element.

The heating element 308 may be positionable about the furnace tube 304. For example, the heating element 308 may be supported by rollers 309 to enable movement thereof back and forth on the support 302 and over the furnace tube 304 along a longitudinal axis of the furnace tube 304. For example, FIG. 3A illustrates the heating element 308 positioned in a retracted position and FIG. 3B illustrates the heating element 308 positioned over the furnace tube 304 in a heating position.

In the illustrated embodiment, the heating element 308 is substantially cylindrical and may partially enclose the furnace tube 304. However, other configurations may be employed that depart from the illustrated cylindrical configuration. The heating element 308 may extend circumferentially about the furnace tube 304 and apply uniform heating thereto. Because the heating element 308 is positionable in the heating position and the retracted position, the workpiece (shown supported on a tray 324) may be heated and rapidly cooled by retraction of the heating element 308. Such rapid cooling is difficult in a conventional vacuum-chamber furnace without purging the chamber with a cooling gas. However, even high-purity inert gases (e.g., argon) still include one or more of hydrogen, nitrogen, or oxygen impurities that may be present in an amount sufficient to embrittle the tantalum alloys disclosed herein.

An interlock assembly 310 may be disposed at and proximate to the open end 306b (FIG. 3C) of the furnace tube 304 to provide access to the inside of the furnace tube 304 so that a workpiece may be disposed therein. The interlock assembly 310 includes an interlock body 312 and a furnace-tube flange 314 extending about a portion of the furnace tube 304. The interlock body 312 may be connected to the furnace-tube flange 314 via one or more fasteners, welding, or another suitable technique. The interlock assembly 310 further includes a cap 318 that may be removable connected to the interlock body 312 to provide or close access to the inside of the furnace tube 304.

The interlock body 312 may include four or more ports (not labeled) that are in communication with the inside of the furnace tube 304. One of the ports may have a vacuum line 320 coupled thereto that is operably coupled to a vacuum pump 322 configured to draw a partial vacuum inside the furnace tube 304. Another port may be coupled to a sensor 323 (e.g., a pressure sensor) configured to measure a vacuum level in the furnace tube 304. Drawing a vacuum inside of the furnace tube 304 allows the heat-treatment process to be conducted in an environment that is substantially free of at least one of oxygen, hydrogen, nitrogen, or other gases that can react and/or embrittle the tantalum alloys disclosed herein, particularly at substantially elevated temperatures.

In practice, the cap 318 may be removed, the workpiece may be placed on the tray 324, the tray 324 may be inserted inside the furnace tube 304 through the interlock assembly 310, and the cap 318 is re-attached to the interlock body 312 by screwing or otherwise securing cap 318 thereto. Once the furnace tube 304 is sealed, a vacuum may be drawn to a sufficient level (e.g., about $10^{-3}$ torr to about $10^{-7}$ torr, or less) using the vacuum pump 322 and the heating element 308 may be subsequently moved to the heating position over the furnace tube 304 and the workpiece supported by the tray 324. Once in the heating position, the heating element 308 may heat the workpiece to a selected heat-treatment temperature and for a selected heat-treatment time, as previously described. After heat treating for the selected temperature and time, the heating element 308 may be moved to the retracted position to allow the heat-treated workpiece to cool rapidly to a temperature at which safe removal of the workpiece may occur without introducing undesirable impurities to it, such as at or below 100° C. A small fan (not shown) may blow cool air or other gas on the furnace tube 304 to improve cooling efficiency, while preventing significant amounts of grain growth in the tantalum alloy upon cooling from the heat-treatment temperature.

In an embodiment, the heating element 308 may be pre-heated to a temperature of about 1100° C. to about 1300° C. The pre-heated heating element 308 may be moved over the furnace tube 304 once the vacuum level detected by the sensor 323 is sufficient. Pre-heating the heating element 308 enables the furnace tube 304 and the workpiece disposed therein to be rapidly heated to the heat-treatment temperature.

FIG. 3C is an enlarged cross-sectional view of the interlock assembly 310 taken along line 3C-3C shown in FIG. 3B, which more clearly shows additional details of the interlock assembly 310. The interlock body 312 may include four ports. Two of the ports are coupled to the vacuum pump 322 and the sensor 323, respectively. Two other ports receive the furnace-tube flange 314 and the cap 318, respectively.

In the illustrated embodiment shown in FIG. 3C, a seal (e.g., an airtight seal) may be formed between the furnace tube 304 and the furnace-tube flange 314 via a pair of seal elements 326 (e.g., o-rings) disposed therebetween. Likewise, a seal may be formed between the furnace-tube flange 314 and the interlock body 312 via a pair of seal elements 328 (e.g., o-rings) disposed therebetween. A seal is provided by securing the cap 318 to the interlock body 312.

It is noted that the furnace system 300 is merely one of many suitable furnaces for heat treating the tantalum-alloy products disclosed herein. Other vacuum-tube furnaces may be employed.

Working Examples of the Present Disclosure

The following working examples of the present disclosure provide further detail in connection with the various embodiments described above for tantalum-alloy products and methods of processing such tantalum-alloy products. The following working examples are for illustrative purposes only and are not meant to be limiting with regard to the scope of the specification or the appended claims.

Figure 4:
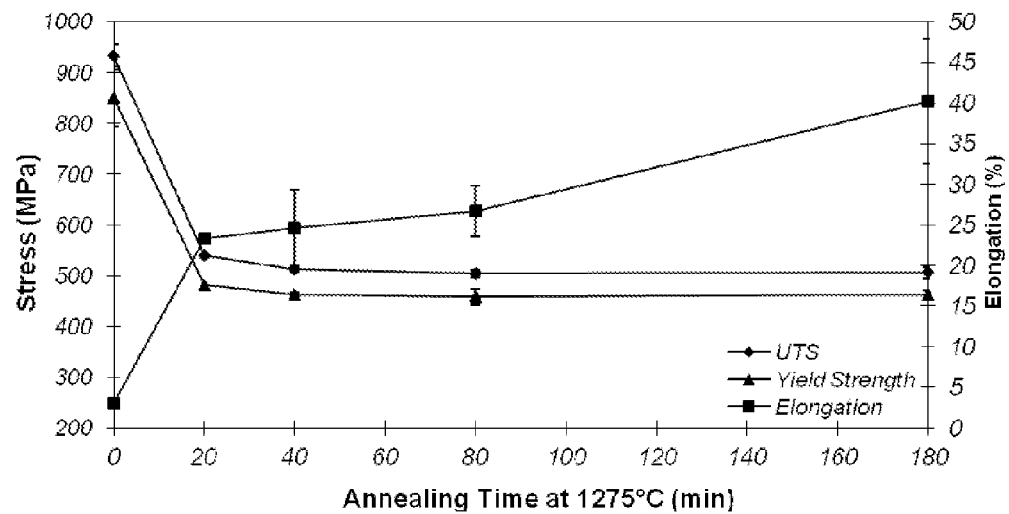
FIG. 4 is a graph of yield strength, ultimate tensile strength, and percent elongation for samples from a first set of tantalum-alloy tubes in the as-drawn and chemically etched condition, after heat treatment at 1275° C. for 0 min, 20 min, 40 min, 80 min, and 180 min.
Figure 5:
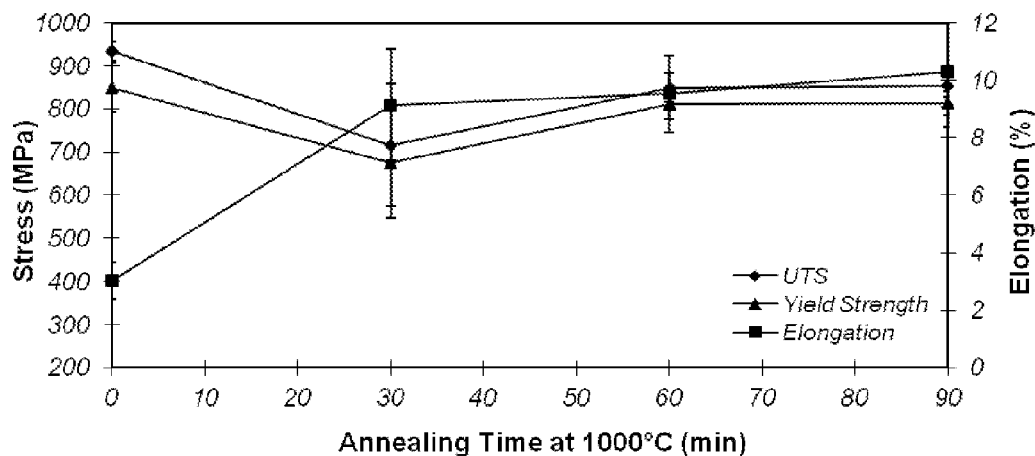
FIG. 5 is a graph of yield strength, ultimate tensile strength, and percent elongation for samples from a second set of tantalum-alloy tubes in the as-drawn and chemically etched condition, and after heat treatment at 1000° C. for 0 min, 30 min, 60 min, and 90 min.
Figure 6:
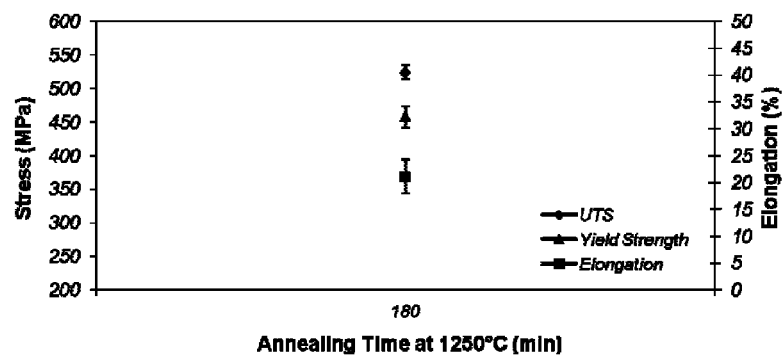
FIG. 6 is a graph of yield strength, ultimate tensile strength, and percent elongation for samples from a third set of tantalum-alloy tubes in the as-drawn and chemically etched condition, after heat treatment at 1250° C. for 180 min.

FIGS. 4-6 illustrate mechanical property test data for samples of different tantalum-alloy tubes and stents cut from such tubes that were subjected to different heat-treatment processes using a furnace system similar to the furnace system 300 shown in FIGS. 3A-3C. The tantalum-alloy tubes were made from a tantalum alloy having about 82.5 wt % tantalum, about 10 wt % niobium, and about 7.5 wt % tungsten. Three different sets of tantalum-alloy tubes were tested, with each set being heat treated at different temperatures. The tubes exhibited about 80% to about 100% cold work after drawing. The tubes were etched in a chemical etching solution (e.g., a solution containing HF and $HNO_3$) prior to heat treating in order to remove an oxide layer present on the tubes. The heat treating was performed in a vacuum furnace, with a vacuum level of about $2\times10^{-5}$ torr prior to subjecting the samples to the heat-treatment temperature. The tantalum-alloy tubes were cooled to about 100° C. after heat treatment before being removed from the furnace. The tantalum-alloy tubes generally had an outer diameter of about 0.190 inch to about 0.1914 inch and a wall thickness of about 0.075 mm to about 0.078 mm. The yield strength, ultimate tensile strength, and percent elongation of the tantalum-alloy tubes were determined by testing in a tensile testing machine. The tensile test parameters were as follows: distance between grips –1.5 inches; gage length –1 inch; pull rate –0.05 inches/minute.

FIG. 4 is a graph of yield strength, ultimate tensile strength, and percent elongation for a total of three samples from the first set of tantalum-alloy tubes in the as-drawn and chemically etched condition after heat treatment at 1275° C. for 0 min, 20 min, 40 min, 80 min, and 180 min. The numerical values for each of the data points are shown below in Table 1.

TABLE 1

| Temp (° C.) | Time (min) | Yield Strength (MPa) | Ultimate Tensile Strength (MPa) | Elongation (%) |
|---|---|---|---|---|
| 0 | 0 | 849 | 934 | 3.0 |
| 1275 | 20 | 482 | 540 | 23.3 |
| 1275 | 40 | 463 | 513 | 24.6 |
| 1275 | 80 | 458 | 504 | 26.7 |
| 1275 | 180 | 461.84 | 505.44 | 40.2 |

The percent elongation to failure in the as-drawn condition was only about 3% or, in some extreme cases, about 1%. The low ductility of the as-drawn sample from the first set was attributed primarily to the high-degree of cold work in the tantalum alloy. The heat-treatment times in FIG. 4 and Table 1 are for the time that the sample was at the heat-treatment temperature and does not include the time that it takes to reach the heat-treatment temperature using the vacuum furnace. It is believed that heat-treatment at 1275° C. produced recrystallization in the tantalum alloy. The ductility increases relatively rapidly with increasing heat-treatment time compared to the yield strength and the ultimate tensile strength. As shown in FIG. 4, the ultimate tensile strength and the yield strength were reduced by an average of about 45% after heat treating at 1275° C. High levels of elongation were reached after only 20 min of heat treatment. Although the precise time at which the grain microstructure of the tantalum alloy in the tantalum-alloy tubes of the second set fully recrystallized was not determined, it is believed that the tantalum alloy was fully recrystallized after 40 min to 80 min of heat treatment at 1275° C. Thus, the heat-treatment at 1275° C. may be characterized as a recrystallization heat treatment.

FIG. 5 is a graph of yield strength, ultimate tensile strength, and percent elongation for a total of 3 samples from a second set of tantalum-alloy tubes in the as-drawn and chemically etched condition, and after heat treatment at 1000° C. for 0 min, 30 min, 60 min, and 90 min. The heat-treatment time in FIG. 5 is the time that the sample was at the heat-treatment temperature and does not include the approximately 14 min that it takes for the sample to reach the heat-treatment temperature using the vacuum furnace. The numerical values for each of the data points are shown below in Table 2.

TABLE 2

| Temp (° C.) | Time (min) | Yield Strength (MPa) | Ultimate Tensile Strength (MPa) | Elongation (%) |
|---|---|---|---|---|
| 0 | 0 | 849 | 934 | 3.0 |
| 1000 | 30 | 676 | 716 | 9.1 |
| 1000 | 60 | 810 | 849 | 9.5 |
| 1000 | 90 | 8132 | 852 | 10.3 |

As shown in FIG. 5, the yield strength and ultimate tensile strength of the tantalum-alloy tubes heat treated at 1000° C. decreases initially and then begin to rise with increasing heat-treatment time from the as-drawn condition and appears to plateau at the higher heat-treatment times. It is believed that off-gassing of dissolved hydrogen, oxygen, and/or nitrogen is the cause for the initial increase in ductility in response to heat treatment. Thus, in the as-drawn condition, it is believed that chemical impurities introduced during the drawing process may cause embrittlement (e.g., hydrogen embrittlement) of the tantalum alloy from which the tantalum-alloy tubes of the second set are made. It is believed that heat-treatment at 1000° C. did not produce recrystallization in the tantalum alloy. Electron backscatter diffraction (EBSD) measurements were performed to confirm that the microstructure of the metal heat treated at 1000° C. was sufficiently misoriented and not recrystallized throughout the cross-section. Thus, the heat-treatment at 1000° C. may be characterized as a stress relief heat treatment.

FIG. 6 is a graph of yield strength, ultimate tensile strength, and percent elongation for samples from a third set of tantalum-alloy tubes in the as-drawn and chemically etched condition, after heat treatment at 1250° C. for 180 min. The heat-treatment time in FIG. 6 is for the time that the sample was at the heat-treatment temperature and does not include the time that it takes to reach the heat-treatment temperature using the vacuum furnace. The numerical values for each of the data points are shown below in Table 3.

TABLE 3

| Temp (° C.) | Time (min) | Yield Strength (MPa) | Ultimate Tensile (MPa) | Elongation (%) |
|---|---|---|---|---|
| 1250 | 180 | 453 | 521 | 21.8 |

FIG. 6 does not include data points for the un-annealed tubing, but it is assumed that the un-annealed tubes are similar. After heat treatment at 1250° C. for 180 minutes, the tubes have properties that are similar to heat treating tubes at 1275° C. for approximately 20 to 80 minutes.

In practice, the tubing used to fabricate an implantable medical device (e.g., a stent or a closure device) may be drawn, etched in a chemical etching solution (e.g., a solution that includes HF and $HNO_3$), and subjected to recrystallization heat treatment (e.g., at about 1250° C. to about 1275° C.) to improve ductility. The etched and heat treated tubes may then be laser cut to form the implantable medical device, etched to, for example, remove features resulting from the laser cutting process, and electropolished to produce a mirror like finish. Finally, the implantable medical devices may be subjected to stress relief heat treatment to remove any cold work and/or any gaseous impurities (e.g., H and/or N) introduced during electropolishing and other manufacturing processes.

Figure 7:
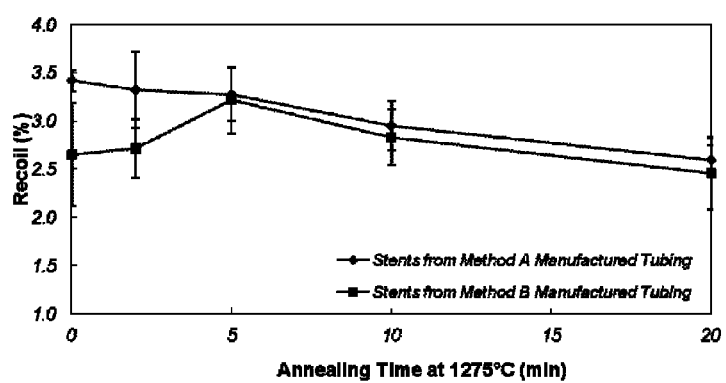
FIG. 7 is a graph of percent radial recoil for stent samples after heat treatment at 1275° C. for 1 second, 2 min, 5 min, 10 min, and 20 min.
Figure 8:
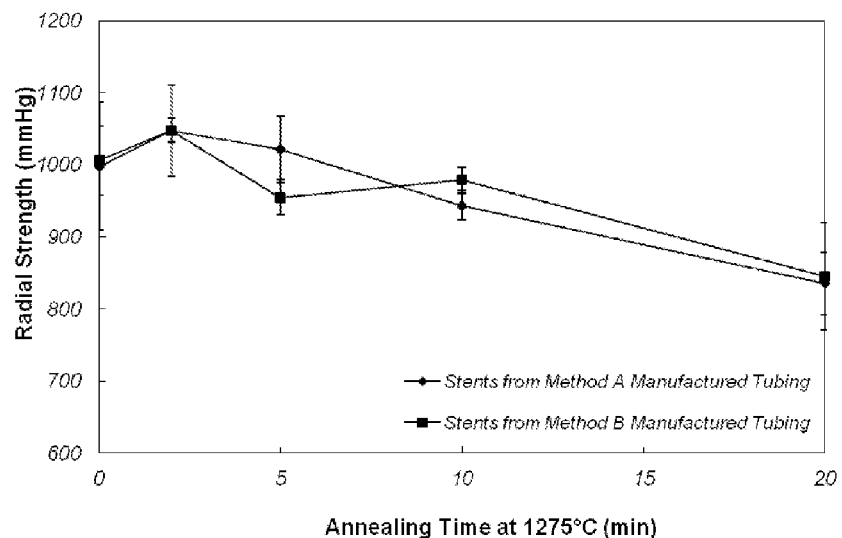
FIG. 8 is a graph of radial strength for stent samples after heat treatment at 1275° C. for 1 second, 2 min, 5 min, 10 min, and 20 min.
Figure 9:
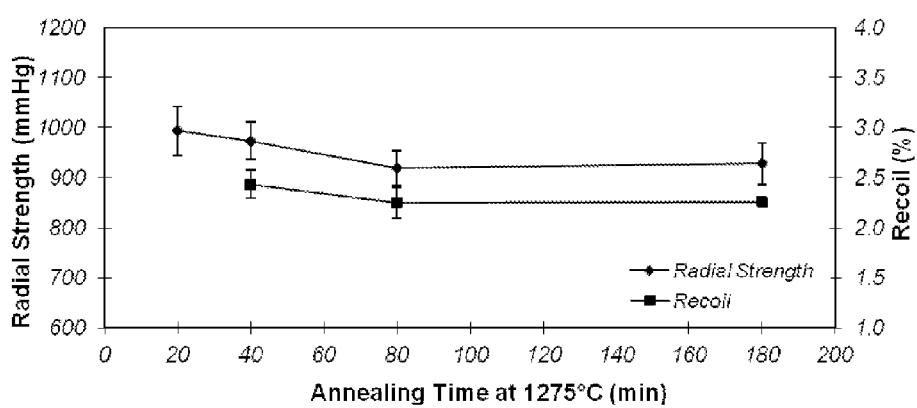
FIG. 9 is a graph of percent recoil and radial strength for stent samples after heat treatment at 1275° C. for 20 min, 40 min, 80 min, and 180 min.
Figure 10:
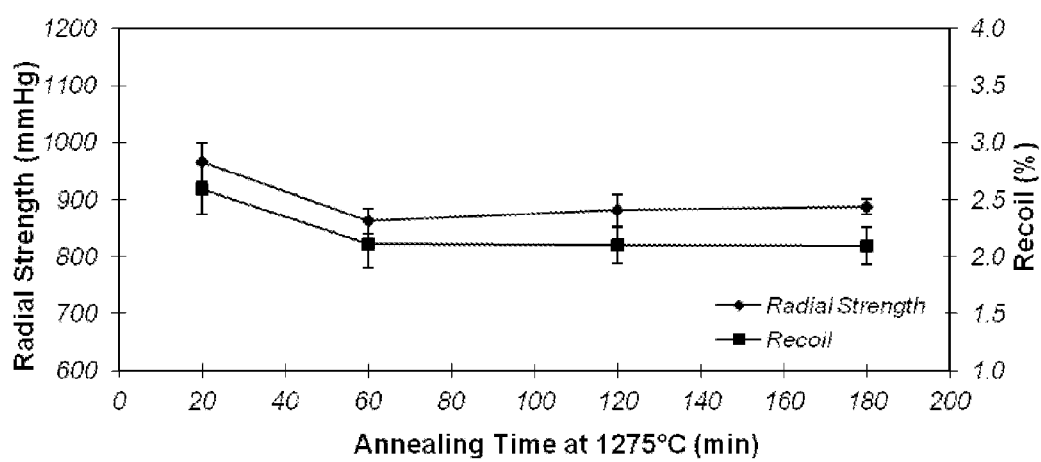
FIG. 10 is a graph of percent recoil and radial strength for stent samples after heat treatment at 1275° C. for 20 min, 60 min, 120 min, and 180 min

Referring to FIGS. 7-10, radial recoil and radial strength measurements after heat treating were also performed on stents laser cut from samples of the first and second sets of tantalum-alloy tubes. FIGS. 7 and 8 relate to a first stent design and FIGS. 9 and 10 relate to a second design, which is similar to the stent 118 shown in FIG. 1B. It was found in the present study that radial recoil and radial strength are affected, at least to a certain extent, by stent design. Each stent was cut using a laser (e.g., a picosecond laser). Each stent was cleaned in 10% Liquinox® for 5 min, double-rinsed in deionized water for 3 min, and etched for 15 min. Any islands present after etching were removed by gentle tapping. After etching, each stent was electropolished in a methanolic electropolishing solution at a temperature of about 8° C. After electropolishing, the stents were, in the case of FIGS. 7 and 8, heat treated at 1275° C. for 1 second, 2 min, 5 min, 10 min, and 20 min. In the case of FIG. 9, the stents were heat treated at 1275° C. for 20 min, 40 min, 80 min, or 180 min. In the case of FIG. 10, the stents were heat treated at 1275° C. for 20 min, 60 min, 120 min, or 180 min. In each case, three stents per heat-treatment time were tested. The vacuum level of the furnace was maintained at about $5\times10^{-6}$ torr. Again, the heat-treatment time in FIGS. 7-10 is the time at the heat-treatment temperature, and does not include the time that it takes for the stent to reach the heat-treatment temperature using the vacuum furnace.

FIG. 7 is a graph of percent radial recoil for stent samples after being heat treated at 1275° C. for 1 second, 2 min, 5 min, 10 min, and 20 min. Each stent sample was crimped on a mandrel, expanded to 3.2 mm outer diameter in an expansion block using a 3.5 mm×18 mm balloon dilatation catheter, and inflated to 22 psi. After inflation, the recoiled outer diameter of each stent sample was measured at three locations along the length thereof. The recoil data for stent samples cut from the second set of tantalum-alloy tubes exhibited a maximum average recoil at 5 min, and the percent recoil decreased thereafter with increasing heat-treatment time. The stent samples cut from the first set of tantalum-alloy tubes had a maximum average recoil at 2 min, and decreased thereafter with increasing heat-treatment time.

FIG. 8 is a graph of radial strength for stent samples after being heat treated at 1275° C. for 1 second, 2 min, 5 min, 10 min, and 20 min. The stent samples utilized for the recoil measurements were subjected to radial strength testing using an MSI radial strength tester. The maximum radial strength for stent samples from the first and second sets of tantalum-alloy tubes occurred at a heat-treatment time of about 2 min.

FIG. 9 is a graph of percent radial recoil and radial strength for stent samples after being heat treated at 1275° C. for 20 min, 40 min, 80 min, or 180 min. The stent samples utilized for the recoil and strength measurements were tested as described above. The recoil data for the stent samples exhibited a maximum average recoil that is presumed to occur at 20 min; although recoil data was not collected for the 20 min time point for this set of stents. The percent recoil decreased thereafter with increasing heat-treatment time. The stent samples had a maximum strength at 20 min, and decreased thereafter with increasing heat-treatment time.

FIG. 10 is a graph of percent radial recoil and radial strength for stent samples after being heat treated at 1275° C. for 20 min, 60 min, 120 min, or 180 min. The stent samples utilized for the recoil and strength measurements were tested as described above. The recoil data for the stent samples exhibited a maximum average recoil at 20 min, with the percent recoil decreasing thereafter with increasing heat-treatment time. The stent samples had a maximum strength at 20 min, and decreased thereafter with increasing heat-treatment time.

Referring to FIGS. 11-16, a microstructural and mechanical property evaluation was also performed on tantalum-alloy stents made from tantalum-alloy tubes having measured amount of tantalum, niobium and tungsten of about 81.3 wt % tantalum, about 12.5 wt % niobium, and about 5.8 wt % tungsten. It is noted that the measured amounts of the metals in the alloy are somewhat of an approximation. The numbers do not add up to 100% and it is possible, for example, that the alloy contains ~0.4 wt % impurities or that the analysis equipment was not sufficiently sensitive to assign exact values for each of the metals. Prior to heat treatment, the stents exhibited about 80% cold work. The stents were heat treated at 1275° C. for 10 min, 20 min, 40 min, 60 min, 80 min, 100 min, and 120 min, with five stent samples per heat-treatment condition. The heat treatment was performed using a furnace system similar to the furnace system 300 shown in FIGS. 3A-3C. Each stent in this study had an outer diameter of about 2.5 mm, a thickness of about 0.230 mm, and a length of about 18 mm. The respective heat-treatment times in FIGS. 9-12 are the times at the heat-treatment temperature and does not include the time that it takes for the sample to reach the heat-treatment temperature using the vacuum furnace.

Figure 11:
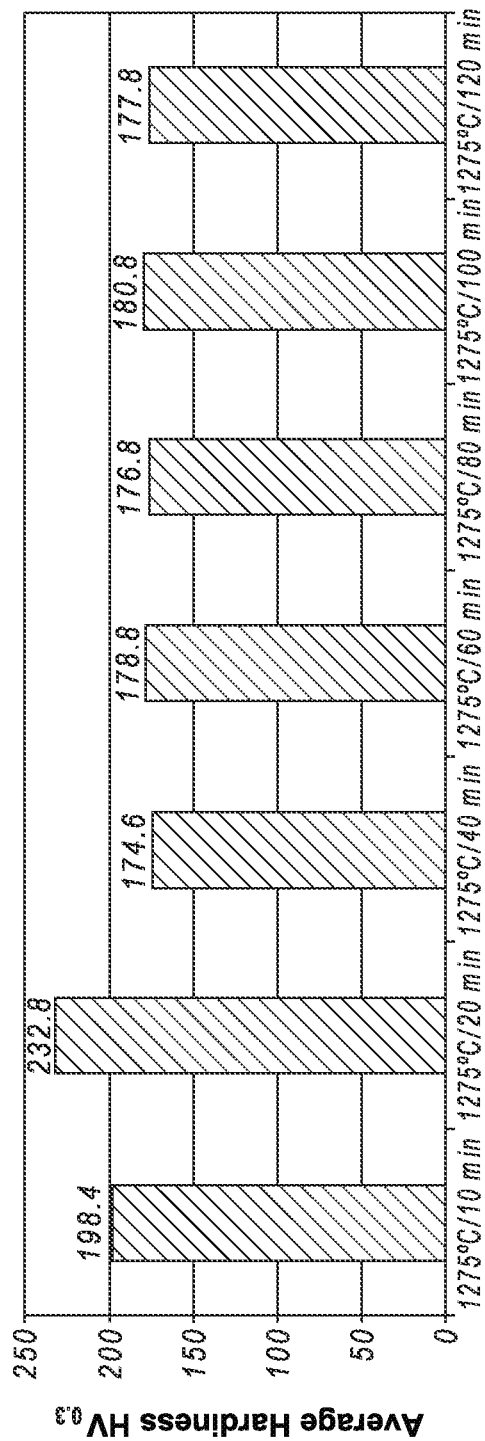
FIG. 11 is a bar chart showing the average Vickers microhardness for stents heat treated at 1275° C. for 10 min, 20 min, 40 min, 60 min, 80 min, 100 min, and 120 min.

FIG. 11 is a bar chart showing the average Vickers microhardness for each heat-treatment condition. After heat-treatment at 1275° C. for about 40 min, the microhardness did not significantly change.

Microstructural analysis in the transverse orientation showed that after heat treatment at 1275° C. for 10 min, the tantalum alloy was only partially recrystallized. After heat treatment at 1275° C. for 20 min, the tantalum alloy was still only partially recrystallized. Complete recrystallization appeared to occur after heat treating at 1275° C. for 40 min, and the average grain size was about 13 μm to about 16 μm in the transverse orientation. Increasing the heat-treatment time past 40 min lead to grain growth, with an average grain size of about 16.1 μm at 100 min and 19.1 μm at 120 min in the transverse orientation.

Figure 12:
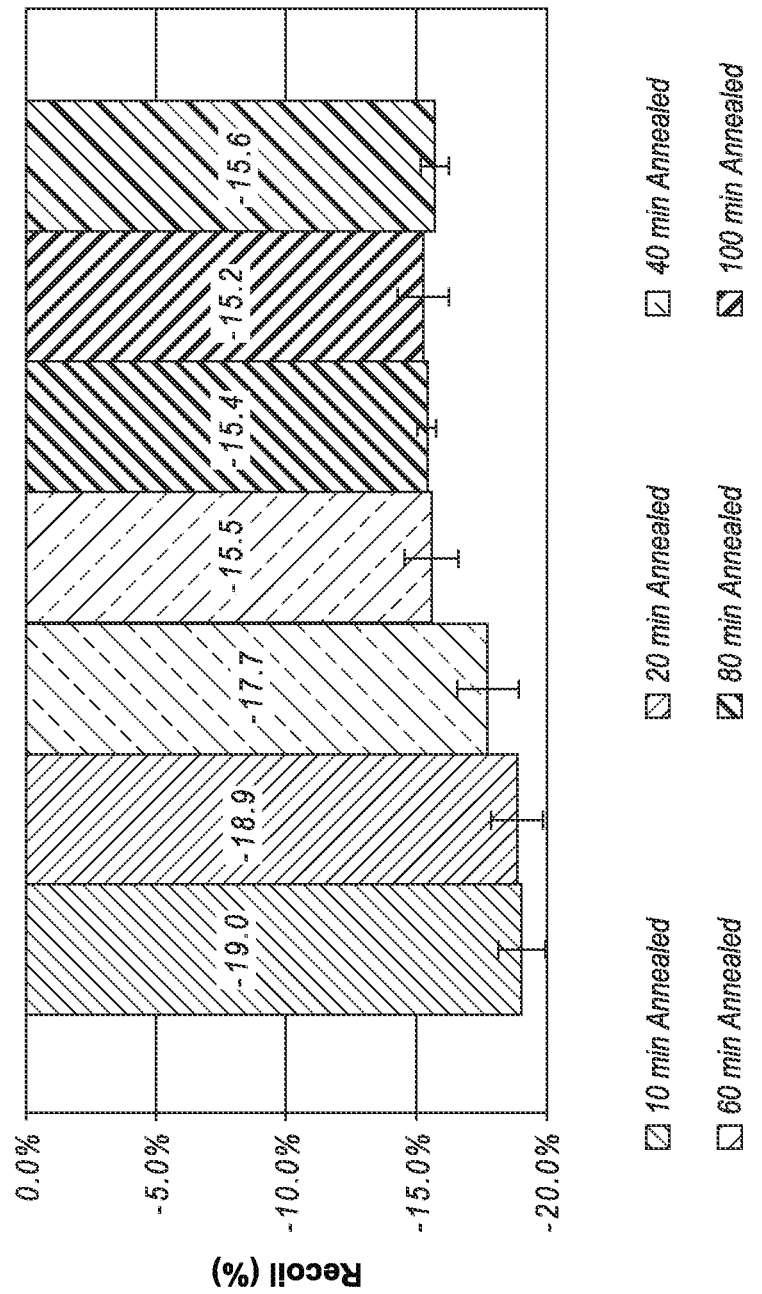
FIG. 12 is a bar chart showing the average crimped recoil when the stents were crimped to an outer diameter of 1.5 mm for the stents heat treated at 1275° C. for 10 min, 20 min, 40 min, 60 min, 80 min, 100 min, and 120 min.
Figure 13:
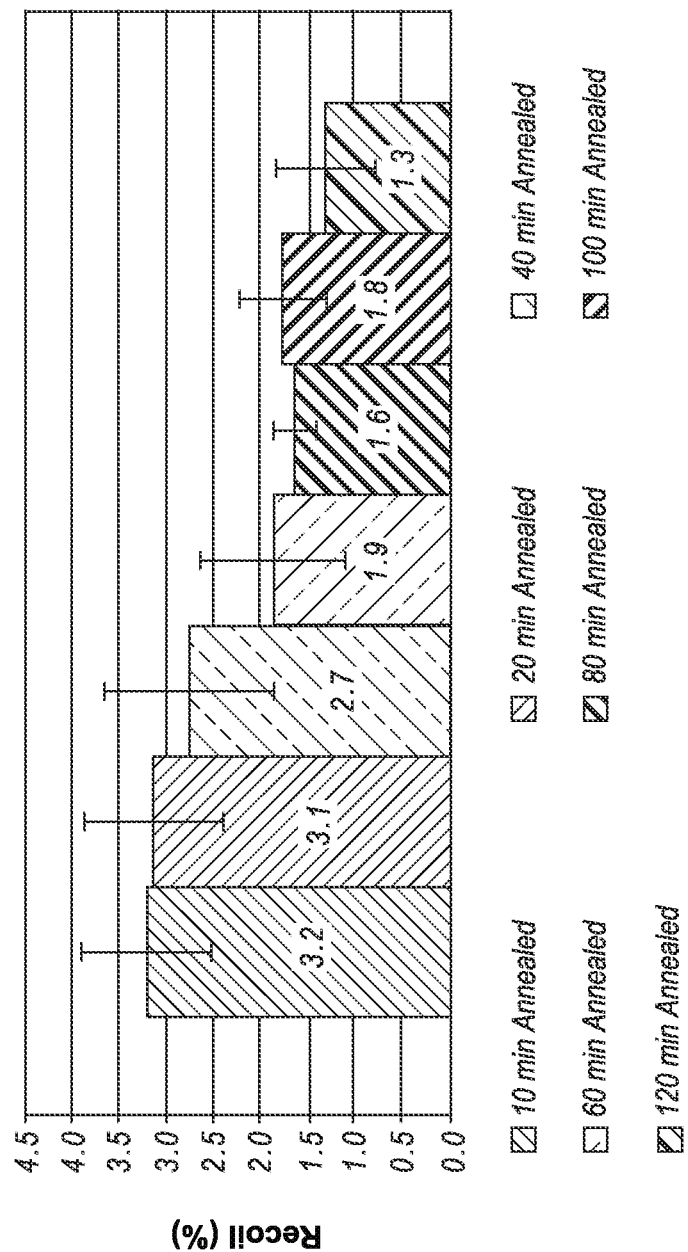
FIG. 13 is a bar chart showing the average recoil when the stents were expanded to an outer diameter of about 7 mm for the stents heat treated at 1275° C. for 10 min, 20 min, 40 min, 60 min, 80 min, 100 min, and 120 min.
Figure 14:
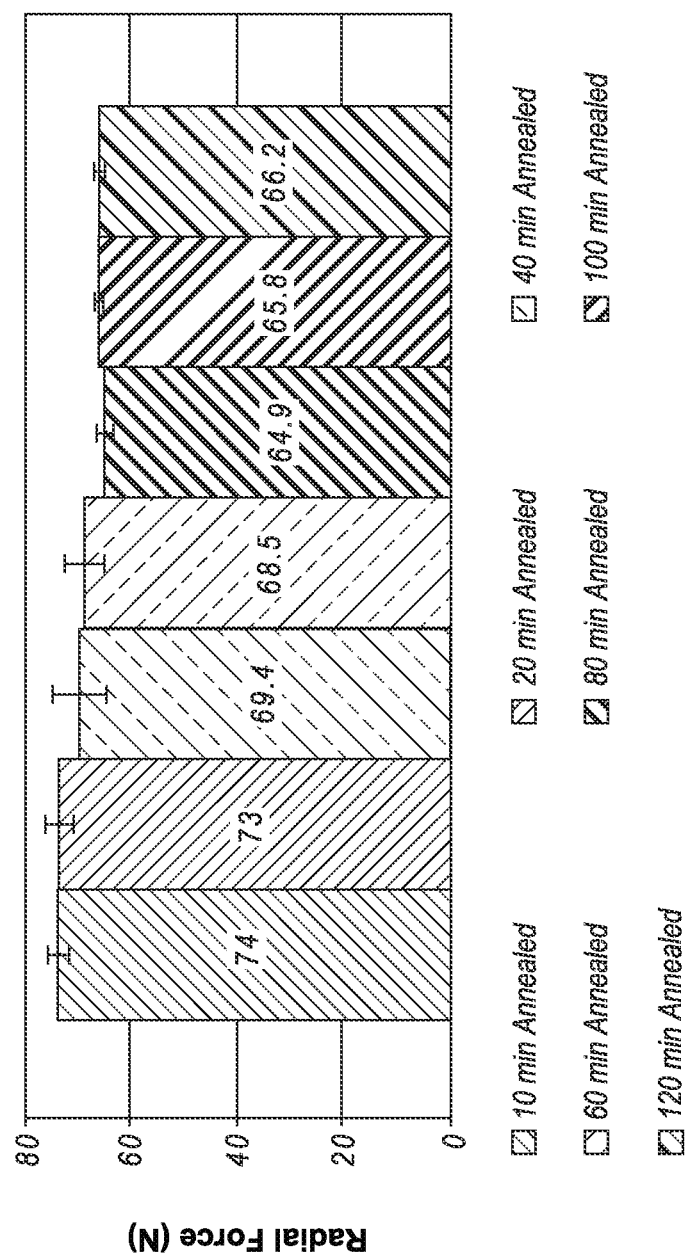
FIG. 14 is a bar chart showing the average radial force necessary to compress the stents from an outer diameter of 2.5 mm to an outer diameter of 1.5 mm for the stents heat treated at 1275° C. for 10 min, 20 min, 40 min, 60 min, 80 min, 100 min, and 120 min.

FIG. 12 is a bar chart showing the average crimped recoil when the stents were crimped to an outer diameter of 1.5 mm for each heat-treatment condition. FIG. 13 is a bar chart showing the average recoil when the stents were expanded to an outer diameter of about 7 mm for each heat-treatment condition. Examination of each stent under a scanning electron microscope showed that the stents did have noticeable cracking at the inner curve of the struts, which will experience the highest stresses. FIG. 14 is a bar chart showing the average radial force necessary to compress the stents from an outer diameter of 2.5 mm to an outer diameter of 1.5 mm for each heat-treatment condition. After heat treatment for 40 min and more, recoil and radial strength properties did not appear to significantly change. In fact, the radial recoil and radial force values tended to decrease, which is currently believed to be due to relieving residual stresses due to cold work.

Figure 15:
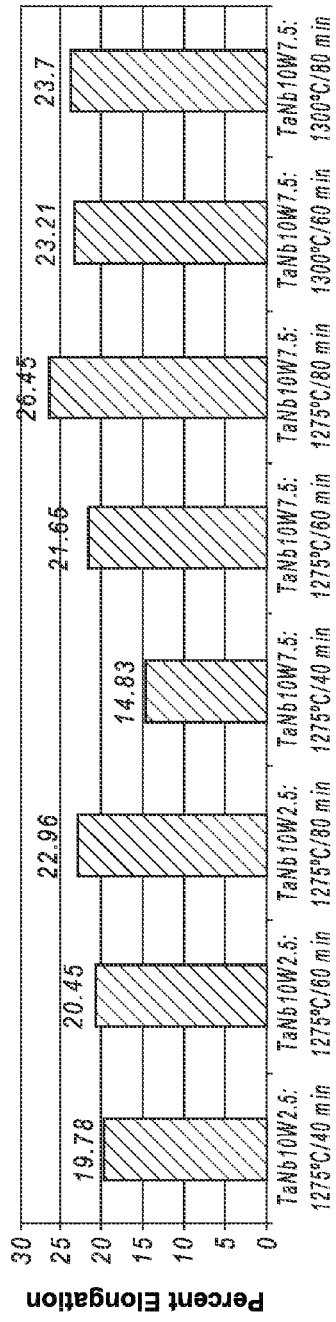
FIG. 15 is a bar chart showing the percent elongation for tantalum-alloy wires of two different composition that were subjected to different heat treatment temperatures and times.
Figure 16:
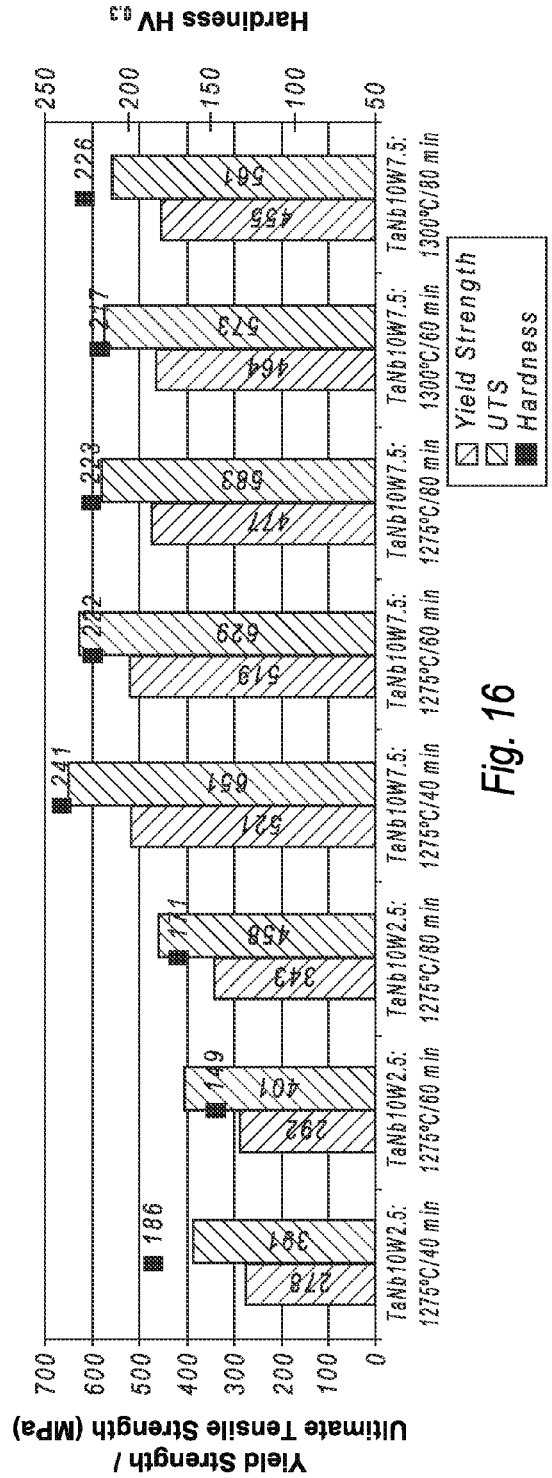
FIG. 16 is a bar chart showing tensile mechanical property data for tantalum-alloy wires of two different composition that were subjected to different heat treatment temperatures and times.

FIGS. 15 and 16 are bar charts showing tensile mechanical property data for tantalum-alloy wires of two different compositions that were subjected to different heat-treatment temperatures and times in a vacuum furnace. The respective heat-treatment times in FIGS. 15 and 16 are the times at the heat-treatment temperature, and do not include the time that it takes for the sample to reach the heat-treatment temperature using the vacuum furnace. The wires were subjected to hardness testing and tensile testing after heat treatment to determine Vickers microhardness, percent elongation, yield strength, and ultimate tensile strength. The wires had a cross-sectional area of 0.30 mm×0.30 mm and exhibited about 80 percent cold work.

The first tantalum alloy composition was about 87.5 wt % tantalum, about 10 wt % niobium, and about 2.5 wt % tungsten and is referred to as TaNb10W2.5 in FIGS. 15 and 16. The second tantalum alloy composition was about 82.5 wt % tantalum, about 10 wt % niobium, and about 7.5 wt % tungsten and is referred to as TaNb10W7.5 in FIGS. 15 and 16. Wires made from the TaNb10W2.5 composition were heat treated at a temperature of 1275° C. for 40 min, 60 min, and 80 min. Wires made from the TaNb10W7.5 composition were heat treated at a temperature of 1275° C. for 40 min, 60 min, and 80 min and also at 1300° C. for 60 min and 80 min.

The embodiments of the present disclosure may be embodied in other specific forms without departing from its spirit or essential characteristics. The described embodiments are to be considered in all respects only as illustrative and not restrictive. Therefore, the scope of the disclosure is indicated by the appended claims rather than by the foregoing description. All changes that come within the meaning and range of equivalency of the claims are to be embraced within their scope.

The invention claimed is:

1. A stent, comprising:
   a stent body including a plurality of struts, at least a portion of the stent body being made from a tantalum alloy including:
   a tantalum content of 77 weight % ("wt %") to 92 wt %;
   a niobium content of 7 wt % to 13 wt %;
   a tungsten content of 1 wt % to 10 wt %; and
   exhibiting at least one mechanical property modified by heat treatment thereof, the at least one mechanical property being at least one of grain microstructure, ductility, yield strength, or ultimate tensile strength, wherein the grain microstructure of the tantalum alloy exhibits an average grain size of 13μm to 16 μm in a transverse orientation.

2. The stent of claim 1, wherein the grain microstructure of the tantalum alloy exhibits recrystallized grains.

3. The stent of claim 2, wherein the grain microstructure of the tantalum alloy is partially recrystallized.

4. The stent of claim 2, wherein the grain microstructure of the tantalum alloy is fully recrystallized.

5. The stent of claim 1, wherein the tantalum alloy is stress relieved, wherein the at least one mechanical property comprises percent elongation, and further wherein the percent elongation is at least 200% greater than prior to being heat treated.

6. The stent of claim 1, wherein the at least a portion of the stent body comprises one or more electropolished surfaces, and wherein the tantalum alloy comprises at least one of hydrogen, oxygen, or nitrogen present in an amount that is not sufficient to cause environmental cracking in the at least a portion.

7. The stent of claim 1, wherein the tantalum alloy is free of at least one of hydrogen, oxygen, or nitrogen.

8. The stent of claim 1, wherein the at least a portion of the stent body comprises one or more etched surfaces, and wherein the tantalum alloy comprises at least one of hydrogen, oxygen, or nitrogen present in an amount that is not sufficient to cause environmental cracking in the at least a portion.

9. The stent of claim 1, wherein the at least a portion of the body comprises one or more etched surfaces, and wherein the tantalum alloy is free of at least one of hydrogen, oxygen, or nitrogen.

10. The stent of claim 1, wherein the tantalum content of the tantalum alloy is 80 wt % to 83 wt %, wherein the niobium content of the tantalum alloy is 9 wt % to 11 wt %, and wherein the tungsten content of the tantalum alloy is 6.5 wt % to 8.5 wt %.

11. The stent of claim 1, wherein the tantalum content of the tantalum alloy is 82.5 wt %, wherein the niobium content of the tantalum alloy is 10 wt %, and wherein the tungsten content of the tantalum alloy is 7.5 wt %.

12. The stent of claim 1, wherein the tantalum content of the tantalum alloy is 87.5 wt %, wherein the niobium content of the tantalum alloy is 10 wt %, and wherein the tungsten content of the tantalum alloy is 2.5 wt %.

13. The stent of claim 1, wherein the tantalum alloy exhibits a tensile elongation of 5% to 50% and a tensile yield strength of 440 MPa to 840 MPa.

14. The stent of claim 1, wherein the tantalum alloy exhibits a tensile elongation of 20% to 50% and a tensile yield strength of 440 MPa to 500 MPa.

15. The stent of claim 1, wherein the tantalum alloy exhibits a tensile elongation of 23% to 27% and a tensile yield strength of 450 MPa to 470 MPa.

16. The stent of claim 1, wherein the stent body exhibits a percent recoil of 2.0% to 3.5% and a radial strength of 845 mm Hg to 1050 mm Hg.

17. The stent of claim 1, wherein the stent body exhibits a percent recoil of 2.0% to 3.5% and a radial strength of 845 mm Hg to 1050 mm Hg, and wherein an average thickness of the plurality of struts is 50 μm to 77 μm.

18. The stent of claim 17, wherein the average thickness of the plurality of struts is 58 μm to 70 μm.

19. A method of fabricating a stent, comprising:
providing a drawn tantalum-alloy product, wherein the drawn tantalum-alloy product comprises a tantalum alloy having a tantalum content of 77 weight % ("wt %") to 92 wt %, a niobium content of 7 wt % to 13 wt %, and a tungsten content of 1 wt % to 10 wt %; and
heat treating the drawn tantalum-alloy product to modify at least one mechanical property of the tantalum alloy, the at least one mechanical property being at least one of grain microstructure, ductility, yield strength, or ultimate tensile strength,
wherein the grain microstructure of the tantalum alloy exhibits an average grain size of 13 μm to 16 μm in a transverse orientation the stent comprises a stent body, the stent body including a plurality of struts, and at least a portion of the stent body is formed from the tantalum-alloy product.

20. The method of claim 19, further comprising etching the drawn tantalum-alloy product in a chemical etching solution to remove an oxide layer from the drawn tantalum-alloy product.

21. The method of claim 20, wherein the etching is performed prior to the heat treating.

22. The method of claim 19, wherein heat treating the drawn tantalum-alloy product to modify at least one mechanical property of the tantalum alloy comprises only partially recrystallizing a grain microstructure of the tantalum alloy.

23. The method of claim 19, wherein heat treating the drawn tantalum-alloy product to modify at least one mechanical property of the tantalum alloy comprises terminating the recrystallization process at a stage where the grain microstructure is fully recrystallized.

24. The method of claim 19, wherein heat treating the drawn tantalum-alloy product to modify at least one mechanical property of the tantalum alloy comprises heating the drawn tantalum-alloy product to a temperature of 1250° C. to 1300° C.

25. The method of claim 19, wherein:
the drawn tantalum-alloy product has been electropolished prior to heat treatment.

26. The method of claim 19, wherein:
the drawn tantalum-alloy product has been chemically etched prior to heat treatment.

27. The method of claim 19, wherein the tantalum alloy of the heat-treated tantalum-alloy product exhibits a tensile elongation of 5% to 50% and a tensile yield strength of 440 MPa to 840 MPa.

28. The method of claim 19, wherein the drawn tantalum-alloy product comprises one or more wires made from the tantalum alloy.

29. A method for implanting a stent into a living subject, the method comprising:
delivering the stent in a delivery device to a selected deployment site within the living subject, wherein the stent comprises: a stent body including a plurality of struts, at least a portion of the stent body being made from a tantalum alloy having a tantalum content of 77 weight % ("wt %") to 92 wt %, a niobium content of 7 wt % to 13 wt %, and a tungsten content of 1 wt % to 10 wt %, and wherein the tantalum alloy exhibits at least one mechanical property modified by heat treatment thereof, the at least one mechanical property being at least one of grain microstructure, ductility, yield strength, or ultimate tensile strength,
wherein the grain microstructure of the tantalum alloy exhibits an average grain size of 13 μm to 16 μm in a transverse orientation;
expanding the stent at the selected deployment site; and
removing the stent from the delivery device.

* * * * *